United States Patent
Shimuta et al.

(10) Patent No.: US 12,193,829 B2
(45) Date of Patent: Jan. 14, 2025

(54) SWALLOWING ANALYZING SYSTEM

(71) Applicant: Murata Manufacturing Co., Ltd., Kyoto (JP)

(72) Inventors: Toru Shimuta, Kyoto (JP); Takayoshi Obata, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 859 days.

(21) Appl. No.: 16/585,161

(22) Filed: Sep. 27, 2019

(65) Prior Publication Data

US 2020/0037947 A1 Feb. 6, 2020

Related U.S. Application Data

(63) Continuation-in-part of application No. PCT/JP2018/011056, filed on Mar. 20, 2018.

(30) Foreign Application Priority Data

Mar. 29, 2017 (JP) ................. 2017-065312

(51) Int. Cl.
*A61B 5/00* (2006.01)
*A61B 5/11* (2006.01)
*A61B 7/02* (2006.01)

(52) U.S. Cl.
CPC .......... *A61B 5/4205* (2013.01); *A61B 5/0002* (2013.01); *A61B 5/11* (2013.01);
(Continued)

(58) Field of Classification Search
CPC ....... A61B 5/11; A61B 5/0002; A61B 5/4205; A61B 5/6822; A61B 2562/0261; A61B 2562/0204; A61B 7/02
See application file for complete search history.

(56) References Cited

U.S. PATENT DOCUMENTS 10,411,181 B2 * 9/2019 Kessler ............... H01L 41/08
2009/0030346 A1 * 1/2009 Kojima ............... A61B 5/6822
600/590
(Continued)

FOREIGN PATENT DOCUMENTS

JP 2008-109950 A 5/2008
JP 2009-60936 A 3/2009
(Continued)

OTHER PUBLICATIONS

Yagi, N. et al. (2016) "A noninvasive swallowing measurement system using a combination of respiratory flow, swallowing sound, and laryngeal motion", Medical & Biological Engineering & Computing, 55(6), pp. 1001-1017 (Year: 2016).*
(Continued)

*Primary Examiner* — Lynsey C Eiseman
*Assistant Examiner* — Amanda L Steinberg
(74) *Attorney, Agent, or Firm* — Pearne & Gordon LLP

(57) ABSTRACT

A swallowing analyzing system (S) includes a swallowing sensor (1) and a swallowing analyzer (30). A piezoelectric film sensor (3) of the swallowing sensor (1) includes a plurality of sensing portions (3A) and (3B) in a longitudinal direction of the neck region. The piezoelectric film sensor (3) is located within a range of movement of thyroid cartilage (103), which occurs along with swallowing, and is attached to skin of an anterior neck region (102). The piezoelectric film sensor (3) individually outputs analog signals (S1a) and (S2a) along with deformation of the plurality of sensing portions (3A) and (3B). A body (20) of the swallowing sensor (1) determines whether the swallowing occurs based on displacement signals that are low frequency components of the analog signals (S1a) and (S2a). The body (20) extracts data on the signals during the (Continued)

swallowing and wirelessly outputs the data to the swallowing analyzer (30).

16 Claims, 12 Drawing Sheets

(52) U.S. Cl.
CPC .............. *A61B 5/6822* (2013.01); *A61B 7/02* (2013.01); *A61B 2562/0204* (2013.01); *A61B 2562/0261* (2013.01)

(56) References Cited

U.S. PATENT DOCUMENTS

| | | | |
|---|---|---|---|
| 2013/0310661 A1* | 11/2013 | Jedwab | A61B 5/4205 600/587 |
| 2016/0143575 A1 | 5/2016 | Oku et al. | |
| 2018/0242900 A1* | 8/2018 | Kuwa | A61B 5/6822 |
| 2020/0121241 A1* | 4/2020 | Hafezi | A61B 5/7475 |

FOREIGN PATENT DOCUMENTS

| | | |
|---|---|---|
| JP | 2009-279122 A | 12/2009 |
| JP | 2012-075758 A | 4/2012 |
| JP | 2013-017694 A | 1/2013 |
| JP | 2014-503330 A | 2/2014 |
| JP | 2016-045816 A | 4/2016 |
| WO | 2015-029501 A1 | 3/2015 |

OTHER PUBLICATIONS

International Search Report for International Application No. PCT/JP2018/011056 dated Jun. 19, 2018.
Written Opinion for International Application No. PCT/JP2018/011056 dated Jun. 19, 2018.

* cited by examiner

SWALLOWING ANALYZING SYSTEM

This is a continuation-in-part of International Application No. PCT/JP2018/011056 filed on Mar. 20, 2018 which claims priority from Japanese Patent Application No. 2017-065312 filed on Mar. 29, 2017. The contents of these applications are incorporated herein by reference in their entireties.

BACKGROUND OF THE DISCLOSURE

Field of the Disclosure

The present disclosure relates to a swallowing analyzing system configured to analyze a swallowing action.

Description of the Related Art

Pneumonia is one of the leading causes of death in Japan. The majority of people who die of pneumonia are elderly people over 65 years old. Aspiration pneumonia is the most frequent pneumonia among elderly people. There are increasing dysphagic patients along with aging society.

Aspiration may be caused by an abnormality of timing in addition to a slowdown in swallowing reflex and muscle weakness. That is, aspiration is likely to occur when swallowing occurs in an inspiratory phase or when an apneic period from the occurrence of swallowing to the resumption of respiration is short. Regarding a relationship between swallowing and a respiratory cycle, it is known that elderly people and Parkinson's disease patients are more likely to swallow in the inspiratory phase than young healthy people, thereby triggering aspiration. Further, those people swallow saliva subconsciously while sleeping. Therefore, aspiration pneumonia is caused by aspiration not only at mealtimes but also during sleep.

Swallowing sensors configured to detect a human swallowing action have been developed for application to diagnosis of the dysphagia. For example, Patent Document 1 discloses a swallowing analyzing system in which swallowing is extracted by using biological sound acquired by an inner ear microphone and a myoelectric potential of the lingual muscle that is acquired by a myoelectric sensor attached to the underjaw. Further, Patent Document 2 discloses a condition detector in which a vibration signal of a living body is acquired by a single sensor (microphone), the acquired vibration signal is separated into a body movement signal and a sound signal, and the condition of the subject is detected based on those signals.

Patent Document 1: Japanese Unexamined Patent Application Publication No. 2016-45816

Patent Document 2: Japanese Unexamined Patent Application Publication No. 2009-279122

BRIEF SUMMARY OF THE DISCLOSURE

Patent Document 1 describes that an arithmetic circuit performs processing up to data extraction and extracted data is transmitted to a server system. In this case, power consumption of a communication circuit can be reduced.

In the swallowing analyzing system described in Patent Document 1, the swallowing is extracted by using the biological sound acquired by the inner ear microphone and the myoelectric potential of the lingual muscle that is acquired by the myoelectric sensor attached to the underjaw. Sound generated along with bloodstream or body movement as well as respiration or utterance is superimposed on the biological sound. Therefore, it is difficult to extract only sound generated along with the swallowing (swallowing sound). Further, a sound signal having a frequency up to 2000 Hz is subjected to frequency analysis and determination is made by using a neural network. Therefore, the computational load on the arithmetic circuit is significant. Thus, it is difficult to reduce the size and the total power consumption.

In addition, many muscles are located at the jaw or neck region. Therefore, a myoelectric potential is generated if the jaw, mouth, or neck is moved or a force is exerted. Thus, it is difficult to distinguish this myoelectric potential from the myoelectric potential of the lingual muscle. As a result, it is difficult to extract the swallowing with high accuracy even if two signals of the biological sound and the myoelectric potential are combined. Body movement or the like other than the swallowing may erroneously be extracted frequently.

Further, the history of swallowing analysis is short and the analysis method has not been established yet. Every time the analysis method is revised, the analysis method in the arithmetic circuit needs to be changed. Therefore, the biological sensor having the arithmetic circuit mounted thereon needs to have a structure in which software can be updated. Thus, there is a tendency of difficulty in use of a device having a small size and a limited communication function.

In the condition detector described in Patent Document 2, devices other than the microphone attached to the neck region are connected to a condition measuring unit by a cable. Therefore, there is a possibility that the hand or the like is caught on the cable and the microphone detaches from the skin. Thus, the behavior of the patient is limited. Further, there is a risk that the microphone is pulled and detaches from the skin due to the weight of the cable or the like. In addition, the condition detector described in Patent Document 2 performs time-frequency analysis for sound having a frequency component with a frequency of at least several kilohertz. Therefore, there is a problem that even short-time data has a large data size.

The present disclosure has been made in view of the problems in the related art described above and it is therefore an object of the present disclosure to provide a swallowing analyzing system capable of extracting data during swallowing with high accuracy.

In order to achieve the object described above, a swallowing analyzing system according to the present disclosure includes a piezoelectric element located within a range of movement of thyroid cartilage, which occurs along with swallowing, and attached to skin of an anterior neck region, a swallowing detector to be driven by an internal battery, configured to make determination for swallowing detection in real time based on a displacement signal that is a low frequency component of a signal outputted from the piezoelectric element, and configured to extract, when the swallowing is detected, data on the signal during the detected swallowing and wirelessly output the data to an outside, and a swallowing analyzer configured to make determination for a swallowing function by receiving the data on the signal during the swallowing.

According to the present disclosure, the data during the swallowing can be extracted with high accuracy.

DETAILED DESCRIPTION OF THE DISCLOSURE

Figure 1:
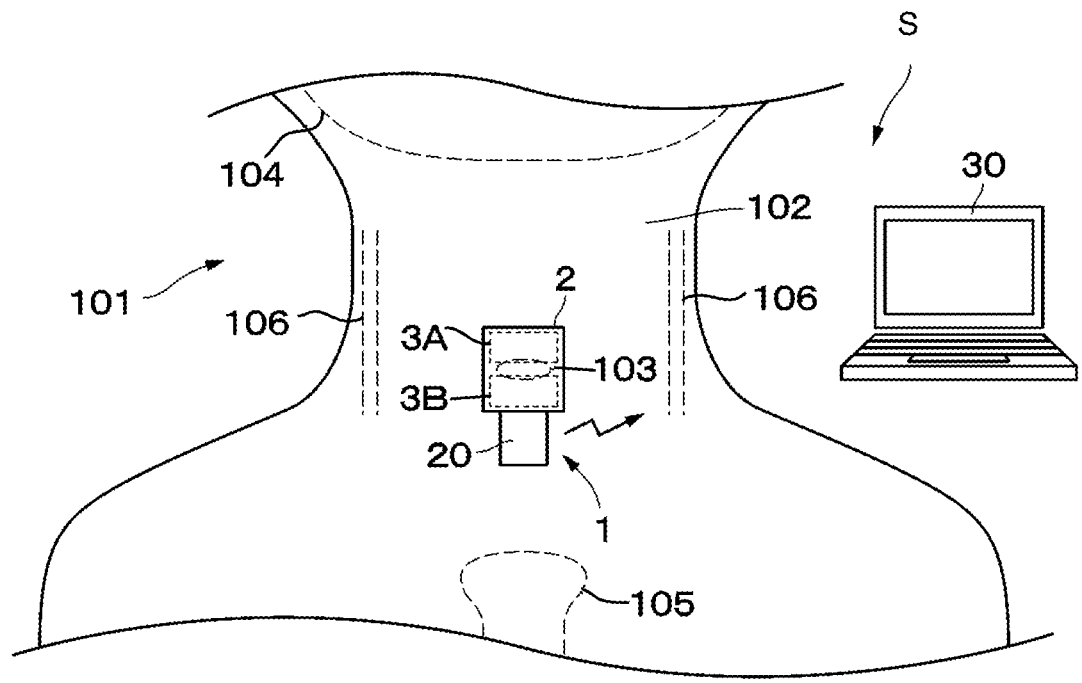
FIG. 1 is an explanatory view illustrating a swallowing analyzing system according to an embodiment of the present disclosure.

A swallowing analyzing system according to an embodiment of the present disclosure is described below in detail with reference to the accompanying drawings.

FIG. 1 to FIG. 5 illustrate a swallowing analyzing system S according to the embodiment of the present disclosure. The swallowing analyzing system S includes a swallowing sensor 1 and a swallowing analyzer 30. The swallowing sensor 1 includes a sensor portion 2 configured to detect swallowing of the subject 101 (human body), and a body 20 configured to process signals outputted from the sensor portion 2.

Figure 2:
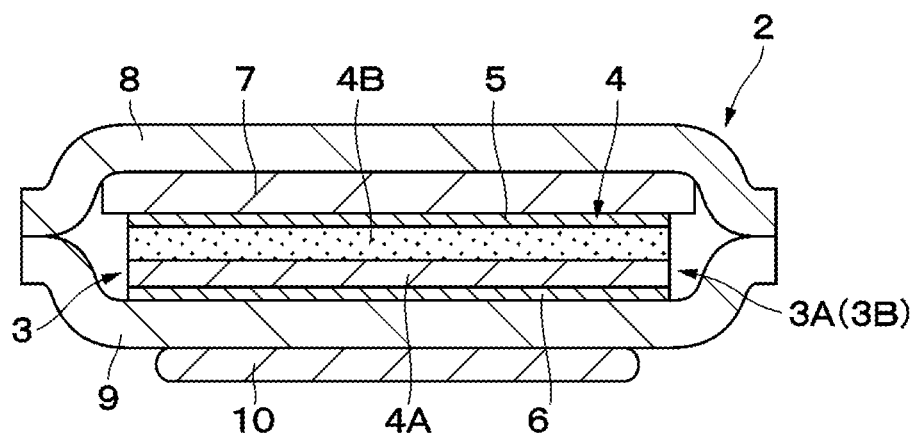
FIG. 2 is a cross-sectional view of a piezoelectric film sensor that is viewed in a direction of arrows II-II in FIG. 3.
Figure 3:
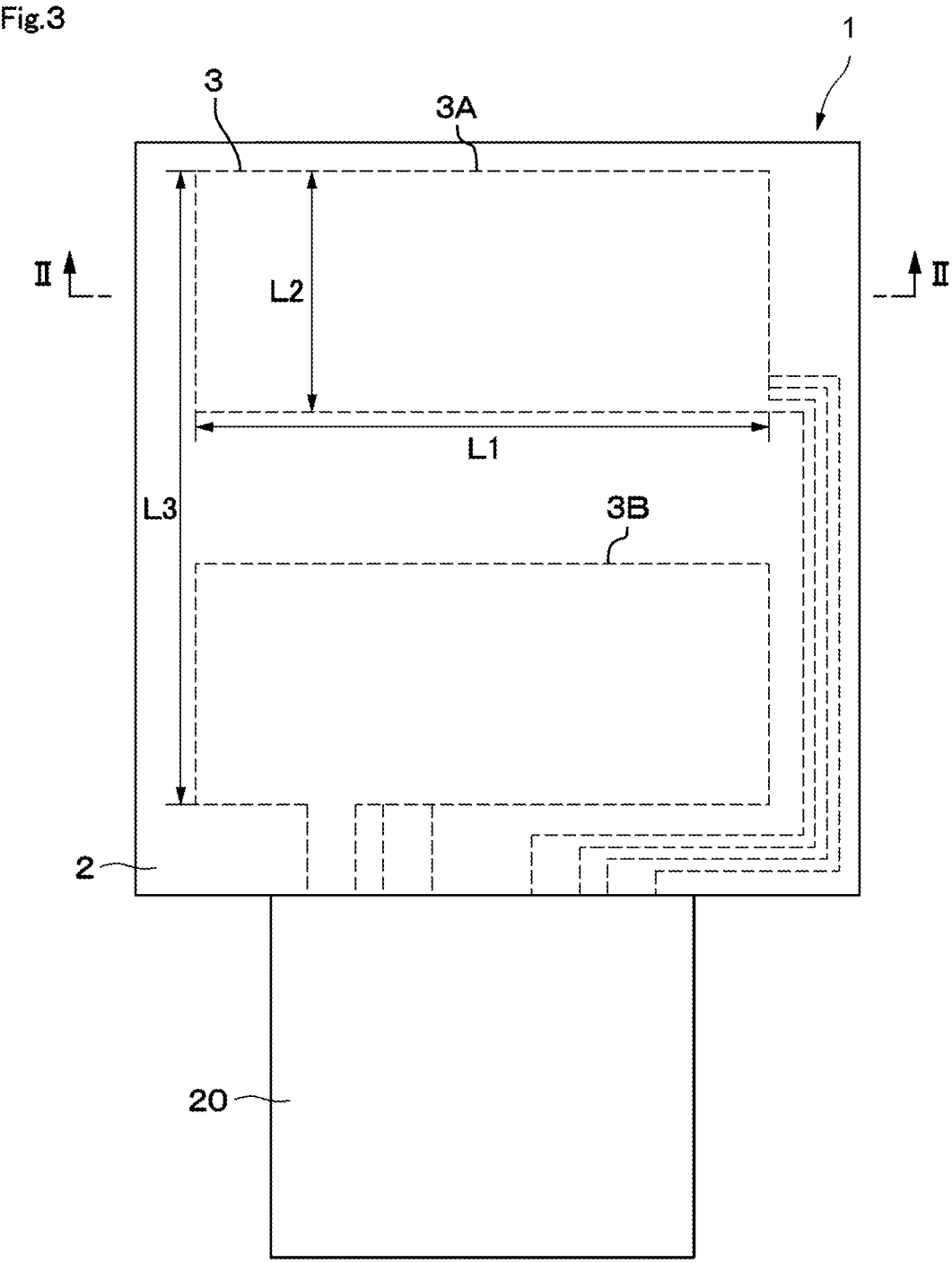
FIG. 3 is a front view illustrating a swallowing sensor of FIG. 1.

For example, the sensor portion 2 as a whole has a rectangular shape and is located on one end side of the swallowing sensor 1 in a vertical direction (upper side in FIG. 3). As illustrated in FIG. 2, the sensor portion 2 includes a piezoelectric film sensor 3, an insulating film 7, and shield films 8 and 9. As illustrated in FIG. 1, the sensor portion 2 is located within a range of movement of thyroid cartilage 103, which occurs along with swallowing, and is attached to the skin of the anterior neck region 102 of the subject 101.

The jawbone 104 is located above the thyroid cartilage 103 and the breastbone 105 is located below the thyroid cartilage 103. A pair of the carotid arteries 106 are located on right and left sides of the thyroid cartilage 103. The sensor portion 2 is arranged within a range in which the sensor portion 2 does not overlap the jawbone 104, the breastbone 105, and the carotid arteries 106. The sensor portion 2 is deformed by displacement of the thyroid cartilage 103 along with swallowing of the subject 101 to detect movement of the thyroid cartilage 103.

The piezoelectric film sensor 3 is an example of a piezoelectric element. The piezoelectric film sensor 3 is located inside the sensor portion 2. The piezoelectric film sensor 3 is formed into a film shape and generates electric signals (electric charges) depending on its deformation.

As illustrated in FIG. 3, the piezoelectric film sensor 3 includes a plurality of (for example, two) sensing portions 3A and 3B (sensing regions). The number of sensing portions is not limited to two and may be three or more but is generally about two to four. The number of sensing portions may be one.

The sensing portions 3A and 3B are arrayed in a longitudinal direction of the neck region (vertical direction) in a state in which the piezoelectric film sensor 3 is attached to the anterior neck region 102 of the subject 101. Specifically, the sensing portions 3A and 3B are arranged in the vertical direction across the thyroid cartilage 103. Therefore, the upper sensing portion 3A is arranged above the thyroid cartilage 103. The lower sensing portion 3B is arranged below the thyroid cartilage 103. The sensing portions 3A and 3B are electrically isolated from each other and individually output signals (analog signals S1$a$ and S2$a$).

As illustrated in FIG. 3, a lateral dimension L1 of each of the sensing portions 3A and 3B is desirably, for example, 5 mm or more and 50 mm or less. A vertical dimension L2 of each of the sensing portions 3A and 3B is desirably, for example, 5 mm or more and 15 mm or less. The total vertical dimension of the plurality of sensing portions 3A and 3B, that is, a vertical dimension L3 of the entire piezoelectric film sensor 3 is desirably, for example, 20 mm or more and 45 mm or less. The lateral dimension L1, the vertical dimension L2, and the like of the sensing portions 3A and 3B are set in consideration of the following matters.

In one swallowing action, the thyroid cartilage 103 ascends by about 20 mm from a position before the swallowing action, moves forward, and then descends back to the original position (see FIG. 6 to FIG. 9). Therefore, the vertical dimension L3 of the piezoelectric film sensor 3 is set to 20 mm or more. If the maximum of four sensing portions are assumed, the vertical dimension L2 of one sensing portion is preferably 5 mm or more.

In addition, the movement of the thyroid cartilage 103 needs to fall out of a range of one sensing portion. Therefore, the vertical dimension L2 of one sensing portion is set to, for example, 15 mm or less as a value smaller than 20 mm.

Further, the distance from the thyroid cartilage 103 to the jawbone 104 is about 50 mm depending on the orientation of the face. The distance from the thyroid cartilage 103 to the breastbone 105 below the thyroid cartilage 103 is about 45 mm. Therefore, the vertical dimension of the entire swallowing sensor 1 including the piezoelectric film sensor 3 and the body 20 is set to 95 mm or less. Thus, an attachment member 10 for fixing the piezoelectric film sensor 3 and the body 20 is arrangeable so as not to overlap the jawbone 104 and the breastbone 105 in the vertical direction. Accordingly, it is possible to suppress detection of vibration noise and to reduce the occurrence of a case in which the attachment member 10 peels off.

Upward displacement of the skin around the breastbone 105 during an action of turning the face upward is smaller than that of the skin around the thyroid cartilage 103. Thus, if the region where the piezoelectric film sensor 3 is attached reaches the vicinity of the breastbone 105, the accuracy of distinction between the action of turning the face upward and swallowing decreases. The body 20 including amplification circuits 21A and 22A and the like is harder and heavier than the piezoelectric film sensor 3. Therefore, the body 20 is desirably arranged below or on the side of the piezoelectric film sensor 3 so as not to hinder the deformation of the flexible piezoelectric film sensor 3. If the body 20 is attached to the skin and if the body 20 overlaps the breastbone 105, the accuracy of distinction between the action of turning the face upward and swallowing decreases as well. The size of the body 20 is about 15 mm or more due to the sizes of internal components such as a battery 26.

Further, the skin around the jawbone 104 is likely to sag. In particular, the skin of elderly people sags greatly. If the piezoelectric film sensor 3 is attached to the sagging skin, it is difficult to transfer the movement of the thyroid cartilage 103 to the piezoelectric film sensor 3 due to the sag of the skin. Therefore, it is desirable to avoid attaching the piezoelectric film sensor 3 around the jawbone 104. Thus, the vertical dimension L3 of the entire piezoelectric film sensor 3 is preferably set to 45 mm or less.

In this structure, the swallowing sensor 1 is arranged so that the center of the piezoelectric film sensor 3 overlaps the laryngeal prominence that is a projection of the thyroid cartilage 103 and the plurality of sensing portions 3A and 3B are arrayed in the vertical direction. Assuming this arrangement, the lateral dimension of the piezoelectric film sensor 3 (sensing portions 3A and 3B) is set to 5 mm or more.

The relative distance between the sternocleidomastoid muscles located on right and left of the thyroid cartilage 103 is about 60 to 100 mm. Upward displacement of the skin on the sternocleidomastoid muscles during the action of turning the face upward is smaller than that of the skin around the thyroid cartilage 103. Thus, if the region where the piezoelectric film sensor 3 is attached reaches the vicinity of the sternocleidomastoid muscles, the accuracy of distinction between the action of turning the face upward and swallowing decreases. Therefore, the lateral dimension of the piezoelectric film sensor 3 is set to 50 mm or less so that the piezoelectric film sensor 3 does not overlap the skin on the sternocleidomastoid muscles.

As illustrated in FIG. 2, the piezoelectric film sensor 3 (sensing portions 3A and 3B) is formed by using a piezoelectric film 4. Specifically, the piezoelectric film sensor 3 is formed of the piezoelectric film 4 and first and second electrode films 5 and 6.

The piezoelectric film 4 is formed by forming a thin piezoelectric film 4B on a base 4A made of an insulating material. For example, a polyimide film is used for the base 4A but other resin films made of polyethylene terephthalate (PET) or the like may be used. Polyimide has a high heat resistance as the resin film and is therefore resistant to a temperature increase during film formation and also resistant to a temperature increase caused by soldering, thermocompression bonding, or the like for attaining electrical connection. Therefore, polyimide is preferably used as the material for the base 4A.

For example, aluminum nitride (AlN) is used for the thin piezoelectric film 4B but an inorganic material such as zinc oxide (ZnO), lead zirconate titanate (PZT), or potassium sodium niobate (KNN) may be used. Further, a piezoelectric polymer film made of polyvinylidene difluoride (PVDF) or polylactide (PLLA) may be used as the piezoelectric film 4.

The first and second electrode films 5 and 6 are provided on both sides (front side and back side) of the piezoelectric film sensor 3 in its thickness direction. The first electrode film 5 is provided on the front surface (one principal surface) of the piezoelectric film 4 while covering the thin piezoelectric film 4B of the piezoelectric film 4. The second electrode film 6 is provided on the back surface (other principal surface) of the piezoelectric film 4 while covering the base 4A of the piezoelectric film 4.

A metal material such as gold (Au), silver (Ag), copper (Cu), aluminum (Al), nickel (Ni), or titanium (Ti) is used for the first and second electrode films 5 and 6 but a conductive material such as indium tin oxide (ITO) may be used, or carbon or the like may be used. The first and second electrode films 5 and 6 detect the analog signal S1a or S2a depending on the deformation of the piezoelectric film sensor 3 (sensing portion 3A or 3B) and output the detected analog signal S1a or S2a to the amplification circuit 21A or 22A of the body 20. In this case, minute deformation is detected and therefore the first and second electrode films 5 and 6 are preferably soft and thin.

The insulating film 7 covers the first electrode film 5. Therefore, the first electrode film 5 is sandwiched between the insulating film 7 and the thin piezoelectric film 4B of the piezoelectric film sensor 3. For example, the insulating film 7 is formed into an elastically deformable film shape by using an insulating soft resin material. The insulating film 7 covers the entire first electrode film 5 to insulate the first electrode film 5 from the shield films 8 and 9.

The shield films 8 and 9 are located on an outer side portion (outer shell) of the sensor portion 2 and are provided on both sides of the piezoelectric film sensor 3 and the insulating film 7 in the thickness direction. That is, the shield films 8 and 9 cover the piezoelectric film sensor 3 and the insulating film 7 from both sides in the thickness direction. The shield films 8 and 9 only need to have conductivity, and a film obtained by forming a thin metal film on a resin film, a conductive resin film, a conductive fabric (nonwoven fabric) produced by using conductive yarns, or the like is suited to each of the shield films 8 and 9. Each of the shield films 8 and 9 is formed into an elastically deformable film shape. The shield films 8 and 9 shield the piezoelectric film sensor 3 from external electromagnetic noise. The shield films 8 and 9 are connected to a ground (GND) of an electric circuit provided in the body 20.

The attachment member 10 is located on one side of the swallowing sensor 1 in the thickness direction. For example, the attachment member 10 is formed into a rectangular shape by using a double coated tape having biocompatibility. The attachment member 10 attaches the swallowing sensor 1 to the surface of the anterior neck region 102 of the subject 101.

The body 20 is located on the other end side of the swallowing sensor 1 in the vertical direction (the lower side in FIG. 1). The body 20 is driven by the internal battery 26 and separates a signal outputted from the piezoelectric film sensor (piezoelectric element) into a displacement signal that is a low frequency component and a sound signal that is a high frequency component. Then, the body 20 makes determination for swallowing detection in real time based on the displacement signal. When the swallowing is detected, the body 20 extracts data on the displacement signal and the sound signal during the detected swallowing and wirelessly outputs the data to the outside.

Figure 4:
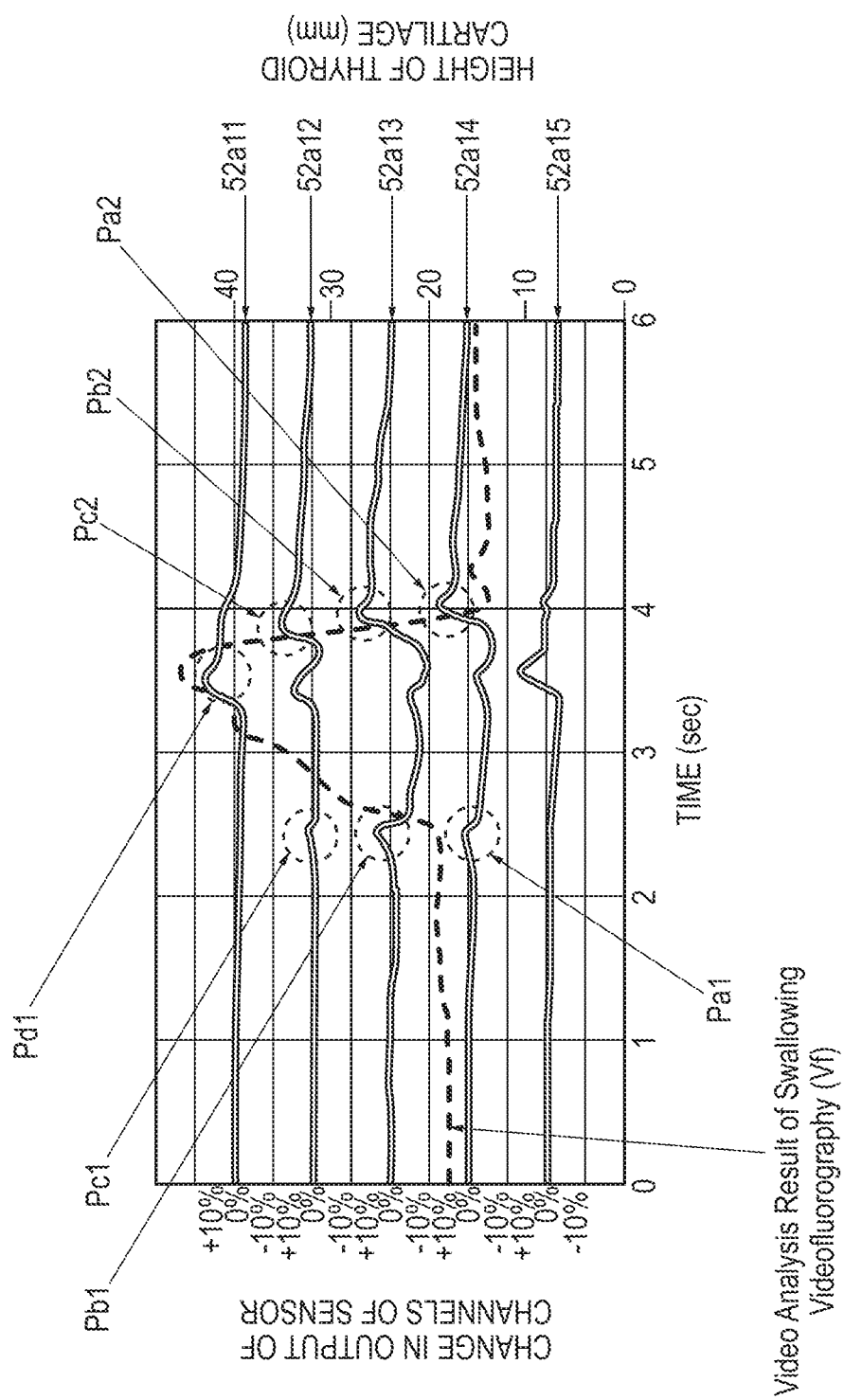
FIG. 4 is a block diagram illustrating the swallowing analyzing system of FIG. 1.
Figure 5:
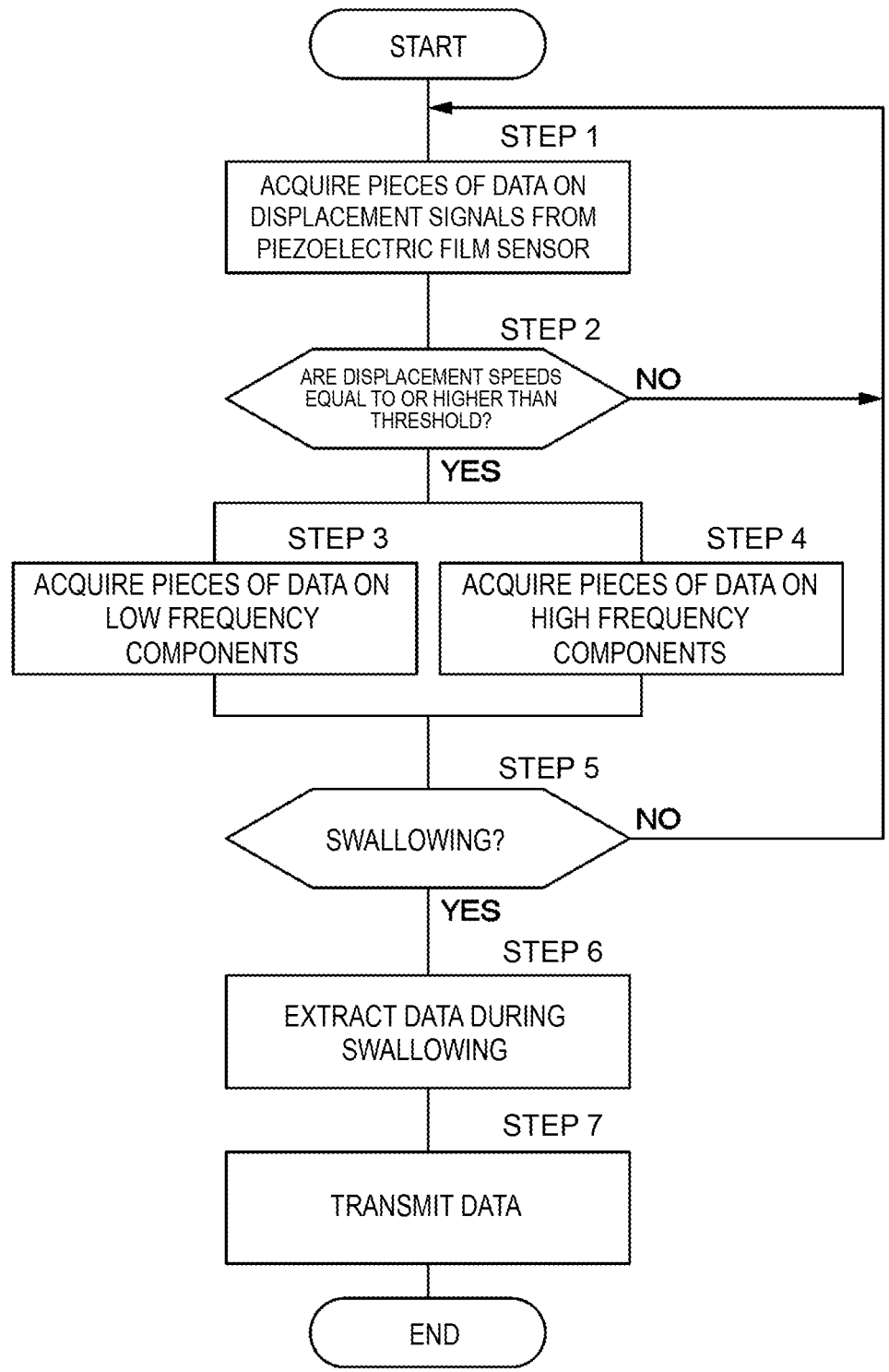
FIG. 5 is a flowchart illustrating swallowing detection processing to be performed by a signal processing unit of FIG. 4.
Figure 6:
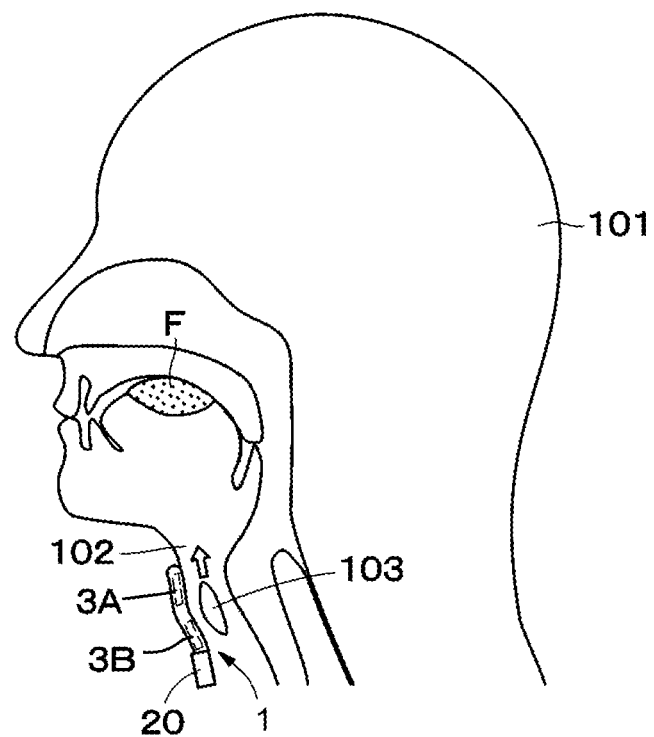
FIG. 6 is an explanatory view illustrating the positional relationships between the thyroid cartilage and the sensing portions of the swallowing sensor in an oral stage.

As illustrated in FIG. 4, the body 20 includes pre-processing units 21 and 22, a signal processing unit 23 (such as a processor), a wireless communication module 25, and the battery 26. In this case, the body 20 is removably connected to the sensor portion 2 by using a connector (not illustrated) or the like and is attached to a lower end side of the sensor portion 2 attached to the subject 101 (see FIG. 3). Thus, if only the sensor portion 2 is damaged or soiled, only the sensor portion 2 can be replaced by being removed from the body 20.

The pre-processing units 21 and 22 are provided for a plurality of systems (for example, two systems) depending on the number of the sensing portions 3A and 3B of the piezoelectric film sensor 3. The pre-processing units 21 and 22 perform amplification, filtering, and A/D conversion as pre-processing for the analog signals S1$a$ and S2$a$ outputted from the piezoelectric film sensor 3. FIG. 1 and FIG. 3 exemplify the case in which the body 20 is arranged below the sensor portion 2. The present disclosure is not limited thereto and the body 20 may be arranged on the side (right or left side) of the sensor portion 2.

The pre-processing unit 21 includes the amplification circuit 21A, a low pass filter 21B (hereinafter referred to as LPF 21B), a high pass filter 21C (hereinafter referred to as HPF 21C), and A/D converters 21D and 21E. An input side of the pre-processing unit 21 is connected to the sensing portion 3A of the piezoelectric film sensor 3 and an output side of the pre-processing unit 21 is connected to the signal processing unit 23.

An input side of the amplification circuit 21A is connected to the sensing portion 3A of the piezoelectric film sensor 3. The amplification circuit 21A amplifies the analog signal S1$a$ outputted from the first and second electrode films 5 and 6 of the sensing portion 3A. The LPF 21B and the HPF 21C separate the amplified analog signal S1$a$ into a low frequency component S1La (displacement speed) and a high frequency component S1Ha (sound) with respect to, for example, several tens of hertz to 100 Hz.

The LPF 21B passes the low frequency component S1La having a frequency lower than a cutoff frequency in the amplified analog signal S1$a$ and attenuates a component having a frequency higher than the cutoff frequency. The low frequency component S1La includes a displacement component associated with a displacement speed of the thyroid cartilage 103 along with swallowing. To make swallowing determination, the low frequency component S1La suffices if the low frequency component S1La is a signal of several tens of hertz or less. Therefore, the cutoff frequency of the LPF 21B is set to, for example, about several tens of hertz to 100 Hz.

The HPF 21C passes the high frequency component S1Ha having a frequency higher than a cutoff frequency in the amplified analog signal S1$a$ and attenuates a component having a frequency lower than the cutoff frequency. The high frequency component S1Ha includes a sound component associated with the sound generated during the swallowing action. Therefore, the high frequency component S1Ha includes at least a signal having a frequency up to about 3 kHz. The cutoff frequency of the HPF 21C is set to, for example, about several tens of hertz to 100 Hz.

The cutoff frequency of the HPF 21C may be set to a value (for example, about 100 to 500 Hz) higher than the cutoff frequency of the LPF 21B within a range in which a necessary sound component such as swallowing sound can be obtained.

The A/D converter 21D converts the low frequency component S1La of the analog signal S1$a$, which is outputted from the LPF 21B, into a digital signal S1Ld. To make the swallowing determination, the displacement signal (displacement speed signal) having a frequency component of several tens of hertz or less is sufficient. Therefore, the sampling frequency of the A/D converter 21D is set to a frequency (for example, about 100 Hz to 1000 Hz) sufficiently higher than that of the low frequency component S1La including the displacement signal of several tens of hertz or less. Since the sampling frequency of the A/D converter 21D is applied to the displacement signal, the sampling frequency of the A/D converter 21D is set to a value (low sampling frequency) lower than a sampling frequency of the A/D converter 21E applied to the sound signal.

The A/D converter 21E converts the high frequency component S1Ha of the analog signal S1$a$, which is outputted from the HPF 21C, into a digital signal S1Hd. To obtain the sound signal, a frequency component having a frequency up to about 3 kHz at the minimum is required for a sampling frequency. Therefore, the sampling frequency of the A/D converter 21E needs to be about 10 kHz. Thus, the sampling frequency of the A/D converter 21E is set to a value (high sampling frequency) higher than the sampling frequency of the A/D converter 21D.

The pre-processing unit 22 is structured substantially similarly to the pre-processing unit 21. Therefore, the pre-processing unit 22 includes the amplification circuit 22A, a low pass filter 22B (hereinafter referred to as LPF 22B), a high pass filter 22C (hereinafter referred to as HPF 22C), and A/D converters 22D and 22E that are substantially similar to the amplification circuit 21A, the LPF 21B, the HPF 21C, and the A/D converters 21D and 21E. An input side of the pre-processing unit 22 is connected to the sensing portion 3B of the piezoelectric film sensor 3 and an output side of the pre-processing unit 22 is connected to the signal processing unit 23.

The amplification circuit 22A amplifies the analog signal S2$a$ outputted from the sensing portion 3B. The LPF 22B and the HPF 22C separate the amplified analog signal S2$a$ into a low frequency component S2La (displacement speed) and a high frequency component S2Ha (sound). The A/D converter 22D converts the low frequency component S2La into a digital signal S2Ld. The A/D converter 22E converts the high frequency component S2Ha into a digital signal S2Hd.

The signal processing unit 23 constitutes a swallowing determination unit configured to make determination for the swallowing action. The signal processing unit 23 is provided in the body 20 and is driven by electric power supplied from the battery 26. An input side of the signal processing unit 23 is connected to the A/D converters 21D, 21E, 22D, and 22E. An output side of the signal processing unit 23 is connected to a memory 24 and the wireless communication module 25. For example, the signal processing unit 23 includes a microcomputer (CPU). The signal processing unit 23 makes determination for swallowing of the subject 101 based on the digital signals S1Ld and S2Ld. When the determination is made for swallowing of the subject 101, the signal processing unit 23 extracts displacement components (digital signals S1Ld and S2Ld) and sound components (digital signals S1Hd and S2Hd) during the detected swallowing and wirelessly outputs the components by using the wireless communication module 25. In addition, the signal processing unit 23 stores the pieces of signal data during the swallowing in the memory 24.

For example, data during swallowing can be set within a data range in which a change in the signal strength of a displacement speed component exceeds a threshold. For example, the data during swallowing may be set within a data range corresponding to a change pattern that matches with a preset reference swallowing pattern (data range from a swallowing start point to a swallowing end point in the reference pattern). Further, the data during swallowing may be set within a data range in which pieces of data during a predetermined time are added prior to and subsequent to one of the two data ranges described above.

The extracted digital signals S1Ld, S2Ld, S1Hd, and S2Hd are wirelessly outputted by using the wireless communication module 25. In addition, the extracted digital signals S1Ld, S2Ld, S1Hd, and S2Hd are stored in the memory 24 (storage unit) provided inside the body 20. The memory 24 may be a volatile memory or a non-volatile memory.

The wireless communication module 25 is provided in the body 20 and is connected to the signal processing unit 23. The wireless communication module 25 includes a modulation circuit configured to modulate signals in conformity with various wireless communication standards, and a transmission unit configured to transmit the modulated signals (neither of which is illustrated). The wireless communication module 25 outputs the digital signals S1Ld, S2Ld, S1Hd, and S2Hd during the swallowing, which are extracted by the signal processing unit 23, toward the swallowing analyzer 30 that is an external device. The swallowing analyzer 30 analyzes a swallowing function based on the received data.

For example, Bluetooth (registered trademark), Wi-Fi (registered trademark), ZigBee (registered trademark), ANT (registered trademark), UWB, or NFC (near-field communication) is applicable to a communication scheme of the wireless communication module 25. In particular, Bluetooth Low Energy (hereinafter referred to as BLE) having low power consumption is preferably used as the communication scheme of the wireless communication module 25. However, BLE is not suited to application in which signals having a large data capacity, such as a sound signal, are transmitted continuously and constantly. To reduce power consumption by using BLE, it is necessary to minimize the transmitted data amount.

Therefore, it is important that only data during swallowing, which is necessary for the swallowing function analysis, be transmitted while being extracted from the sound signal having a large data amount. In consideration of this point, the signal processing unit 23 makes determination for swallowing detection in real time based on the displacement signal and, when the swallowing is detected, extracts data on the displacement signal and the sound signal during the detected swallowing.

If the sound signal having a large data amount is analyzed constantly, power consumption increases compared with the analysis of the displacement signal (displacement speed signal). The signal processing unit 23 makes the swallowing determination based on the displacement signal (displacement speed signal) having a small data amount. Therefore, it is possible to reduce power consumption other than that during communication.

The battery 26 is provided in the body 20 and is connected to the pre-processing units 21 and 22, the signal processing unit 23, the wireless communication module 25, and the like. The battery 26 constitutes a power supply configured to supply drive voltages (electric power) to the amplification circuits 21A and 22A, the A/D converters 21D, 21E, 22D, and 22E, the signal processing unit 23, the wireless communication module 25, and the like.

The swallowing analyzer 30 is structured by an external device such as a PC (computer), a portable terminal, a storage device, or a server (none of which is illustrated). The swallowing analyzer 30 makes determination for the swallowing function by receiving the data on the displacement signal and the sound signal during the swallowing, which is transmitted from the wireless communication module 25. Specifically, the swallowing analyzer 30 makes determination for the swallowing action based on the displacement signal and determines whether swallowing dysfunction such as a slowdown in swallowing reflex or an abnormality of swallowing timing is present based on the sound signal obtained at the time of determination for the swallowing action.

The swallowing analyzing system S has the structure described above. Next, swallowing detection processing in which the signal processing unit 23 detects swallowing of the subject 101 is described with reference to FIG. 5. The swallowing detection processing is repeatedly executed in each predetermined period while the swallowing sensor 1 is driven.

In Step 1, the low frequency components S1La and S2La outputted from the LPFs 21B and 22B are first converted into the digital signals S1Ld and S2Ld by the A/D converters 21D and 22D. The signal processing unit 23 acquires the digital signals S1Ld and S2Ld, which are pieces of data on displacement signals obtained through conversion at a low sampling frequency of, for example, about 100 Hz.

The absolute values of the displacement speeds (digital signals S1Ld and S2Ld) increase along with movement of the throat before the swallowing. Therefore, determination is subsequently made in Step 2 as to whether the absolute values of the displacement speeds are equal to or higher than a predetermined threshold ST based on the digital signals S1Ld and S2Ld that are the displacement signals. When the absolute values of the displacement speeds are lower than the threshold ST, an action before the swallowing is not detected. Therefore, the determination is "NO" in Step 2 and the processing returns to Step 1. When the absolute values of the displacement speeds exceed the predetermined threshold ST, the action before the swallowing is detected. Therefore, the determination is "YES" in Step 2 and the processing proceeds to Steps 3 and 4.

In Step 3, changes in the signal strengths of the sensing portions 3A and 3B are acquired individually. Specifically, waveform patterns of temporal changes in the digital signals S1Ld and S2Ld including the displacement signals are acquired. In Step 4, the high frequency components S1Ha and S2Ha outputted from the HPFs 21C and 22C are converted into the digital signals S1Hd and S2Hd by using the A/D converters 21E and 22E. Then, the signal processing unit 23 starts to acquire the digital signals S1Hd and S2Hd including sound signals.

In Step 5, determination is subsequently made as to whether swallowing occurs based on whether the change patterns of the digital signals S1Ld and S2Ld and timings of changes in the sensing portions 3A and 3B (for example, maximum signal strengths) fall within predetermined ranges.

Figure 13:
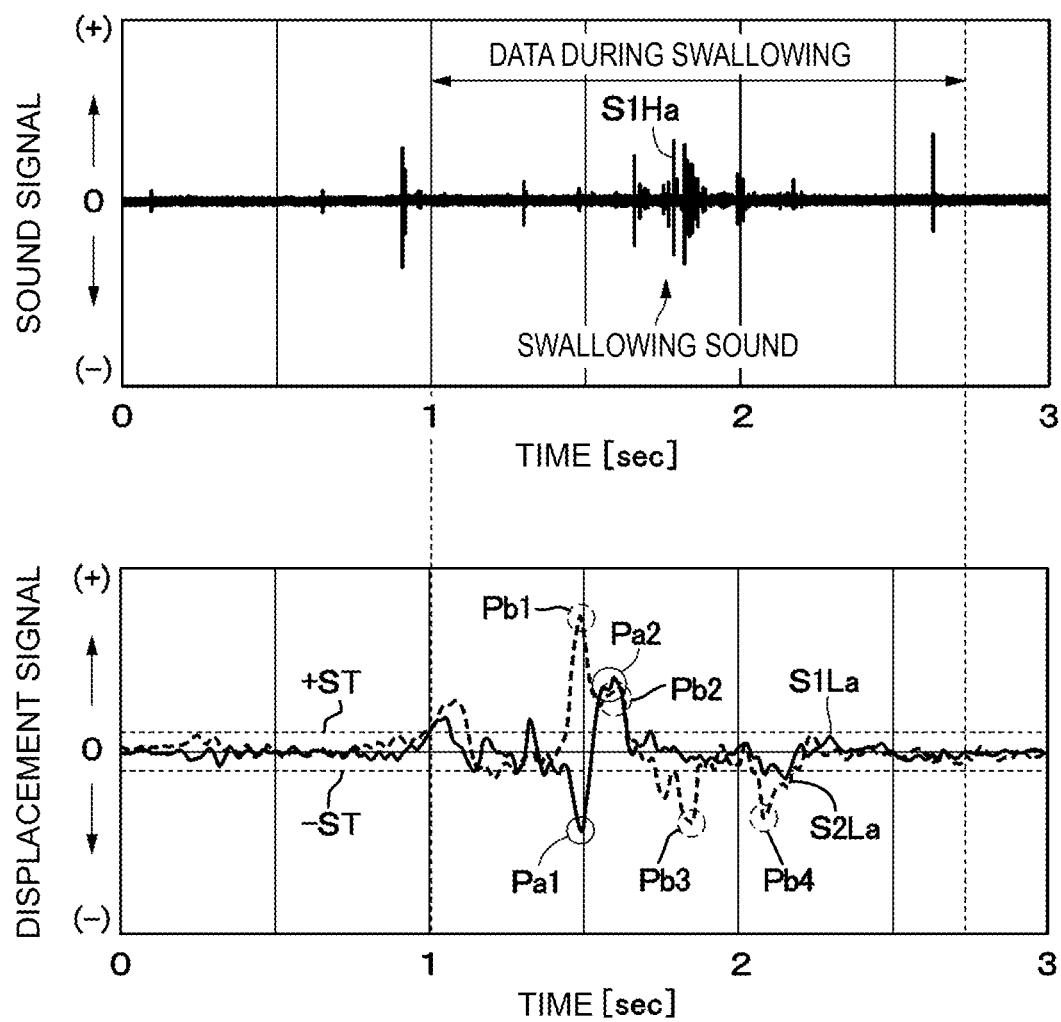
FIG. 13 is a characteristic diagram illustrating an example of displacement signals and sound signals during the swallowing action in the swallowing sensor according to the embodiment of the present disclosure.

FIG. 13 illustrates an example of the waveform patterns during the swallowing. As illustrated in FIG. 13, a sharp downward peak Pa1 of the upper sensing portion 3A and a sharp upward peak Pb1 of the lower sensing portion 3B occur within a predetermined time around 1.5 seconds during the swallowing. Then, a slightly broad upward peak Pa2 of the upper sensing portion 3A and a slightly broad upward peak Pb2 of the lower sensing portion 3B occur within a predetermined time around 1.6 seconds. Further, two gentle downward peaks Pb3 and Pb4 occur within a predetermined time around 1.7 to 2.1 seconds. Therefore, the signal processing unit 23 determines whether the swallowing occurs based on whether all the peaks Pa1, Pa2, and Pb1 to Pb4 occur.

The peaks Pa1 and Pb1 correspond to upward movement (elevation) of the laryngeal prominence. The peaks Pa2 and Pb2 correspond to forward movement (advance) of the laryngeal prominence. The peaks Pb3 and Pb4 correspond to movement of the laryngeal prominence to the original position.

To obtain the sharp downward peak Pa1 of the upper sensing portion 3A and the sharp upward peak Pb1 of the lower sensing portion 3B, it is desirable that the arrangement distance between the upper sensing portion 3A and the lower sensing portion 3B be approximated to the size of the laryngeal prominence in the longitudinal direction of the neck region (about 10 to 35 mm) so that the movement of the thyroid cartilage 103 can easily be grasped on the skin, and the upper sensing portion 3A and the lower sensing portion 3B can be arranged vertically across the laryngeal prominence. When the plurality of sensing portions 3A and 3B are arranged in this manner, determination can be made while distinguishing the upward movement and the forward movement of the laryngeal prominence.

FIG. 13 illustrates the example of the waveform patterns during the swallowing. The number of peaks or the timings of peaks may differ depending on, for example, the attachment position of the piezoelectric film sensor 3, differences in measurement conditions, individual differences, or the degree of dysphagia. Therefore, there is no need to use all the peaks Pa1, Pa2, and Pb1 to Pb4 for the swallowing determination. For example, only the peaks Pa1 and Pa2, which are characteristic and easy to detect, may be used. For example, a peak of the upper sensing portion 3A may also be detected at a time corresponding to the peak Pb3 or Pb4 of the lower sensing portion 3B. Therefore, the swallowing determination may be made in consideration of other peaks as well as the peaks Pa1, Pa2, and Pb1 to Pb4.

Further, the swallowing determination is not limited to the displacement signal, and the sound signal may be taken into consideration. Specifically, determination of whether the swallowing occurs may be made in consideration of, for example, whether swallowing sound is included in the sound signal in addition to whether the determination condition on the displacement signal described above is satisfied.

When the determination condition described above is not satisfied, determination is not made that the swallowing occurs. Therefore, the determination is "NO" in Step 5 and the processing returns to Step 1. When the determination condition described above is satisfied, determination is made that the swallowing occurs. Therefore, the determination is "YES" in Step 5 and the processing proceeds to Step 6, in which only data during the swallowing is extracted.

For example, the data during the swallowing corresponds to pieces of data on the digital signals S1Ld, S2Ld, S1Hd, and S2Hd from a start point to an end point, assuming that the start point is a timing when the action before the swallowing is detected in Step 2 (timing when the absolute values of the displacement speeds exceed the predetermined threshold ST) and the end point is a timing when a predetermined time elapses from the determination in Step 5 that the swallowing occurs.

The predetermined time is set as appropriate in consideration of, for example, individual differences in waveform data among the subjects 101. Further, there is no need to extract all the pieces of data for which acquisition is started in Step 2. For example, the timing of the determination in Step 5 that the swallowing occurs may be set as a reference and data within predetermined time ranges prior to and subsequent to the timing may be extracted. In Step 7, the extracted data is subsequently transmitted to the swallowing analyzer 30 that is the external device by using the wireless communication module 25. In addition, the extracted data is stored in the internal memory 24. If the swallowing analyzer 30 can securely receive the wirelessly transmitted data, the processing of storing the data in the internal memory 24 may be omitted.

According to this embodiment, the body 20 makes determination for swallowing detection by using the displacement signal on the thyroid cartilage 103. Therefore, the accuracy of swallowing determination increases. The body 20 makes determination for swallowing detection based on the displacement signal that is the low frequency component. Therefore, processing performance of high throughput is unnecessary for arithmetic processing in the determination for swallowing detection. Further, the body 20 includes the battery 26 and wirelessly outputs data. Therefore, power supply and data output cables are unnecessary. Thus, the weights of the cables are eliminated, thereby being capable of reducing the occurrence of a case in which the swallowing sensor 1 including the piezoelectric film sensor 3 and the body 20 peels off the skin due to the weight.

Further, the body 20 makes the swallowing determination by processing measurement data. Every time determination is made that the swallowing is detected, the body 20 extracts data on the signals (digital signals S1Ld, S2Ld, S1Hd, and S2Hd) during the swallowing and wirelessly outputs the data to the outside. Therefore, the wirelessly transmitted data is only the data during the swallowing. Thus, there is no need to continuously transmit a large amount of data. Accordingly, it is possible to reduce power consumption of, for example, the wireless communication module 25 and to use a small-size, low-height, and small-capacity battery as the internal battery 26.

Further, the swallowing analysis is performed by the external swallowing analyzer 30 instead of the inside of the body 20 attached to the subject 101. A PC, a terminal, or the like in which internal analysis processing is rewritable may be used as the swallowing analyzer 30. The swallowing analysis method has not been established currently and may be revised later on. Even if the swallowing analysis method is revised, the revised analysis method can be applied easily.

Further, the body 20 acquires data on the displacement signal at a low sampling frequency and, when a change that satisfies a predetermined condition is detected in the data on the displacement signal, acquires data on the sound signal at a high sampling frequency. Therefore, the data amount is normally small and high-speed processing is unnecessary. Thus, the power consumption of the body 20 can be reduced. As a result, a small-capacity battery can be used as the internal battery 26.

Further, when the displacement around the thyroid cartilage 103 starts to occur and a change that satisfies a predetermined condition (for example, the rate of change is equal to or higher than a threshold) starts to be detected in the data on the displacement signal, the body 20 acquires the data on the sound signal at the high sampling frequency. Therefore, the determination for swallowing detection can be made accurately by using not only the data on the displacement signal but also the data on the sound signal.

Further, the body 20 automatically extracts, from the displacement signal and the sound signal, only partial data with strong possibility of the swallowing involving the displacement around the thyroid cartilage 103. For example, even in measurement during sleep, it is possible to exclude unnecessary data indicating that the swallowing does not occur. Thus, there is no need to extract the swallowing from long-time data through ex-post data analysis.

Further, the piezoelectric film sensor 3 is attached to the skin within the range of the movement of the thyroid cartilage 103, which occurs along with the swallowing. Therefore, even if, for example, the thickness and the shape of the neck (neck region) differ among the subjects 101, influence of the individual differences can be suppressed and the sensor can be used without being adjusted to many people.

Further, the piezoelectric film sensor 3 includes the plurality of sensing portions 3A and 3B in the longitudinal direction of the neck region and outputs the signals along with deformation of the plurality of sensing portions 3A and 3B. Therefore, the plurality of sensing portions 3A and 3B can output signals having different waveform patterns in response to the movement (upward movement and forward movement) of the thyroid cartilage 103. By using the analog signals S1$a$ and S2$a$ from the plurality of sensing portions 3A and 3B, the swallowing can be identified more easily than in a case in which a single sensing portion is used.

Further, the piezoelectric film sensor 3 is attached to the skin on the thyroid cartilage 103 and includes the plurality of sensing portions 3A and 3B in the longitudinal direction of the neck region. For example, at the time of nodding or other neck actions that do not cause a change in the relative position between the thyroid cartilage 103 and the skin on the thyroid cartilage 103 (action of vertically moving the head), the relative position between the thyroid cartilage 103 and the skin does not change. At the time of swallowing action, the relative position between the thyroid cartilage 103 and the skin changes.

This point is described in detail with reference to FIG. 6 to FIG. 12. For example, in an oral stage illustrated in FIG. 6, which is a period of a reference posture before the swallowing action, the subject 101 masticates food F and delivers the food F into the pharynx. At this time, the thyroid cartilage 103 is located at a position near the lower sensing portion 3B out of the two sensing portions 3A and 3B.

Figure 7:
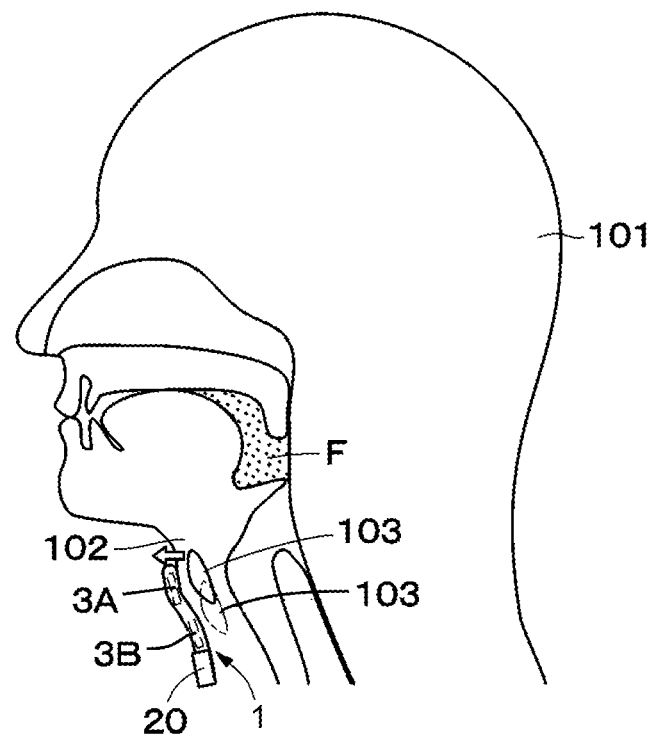
FIG. 7 is an explanatory view illustrating the positional relationships between the thyroid cartilage and the sensing portions of the swallowing sensor in a pharyngeal stage.
Figure 8:
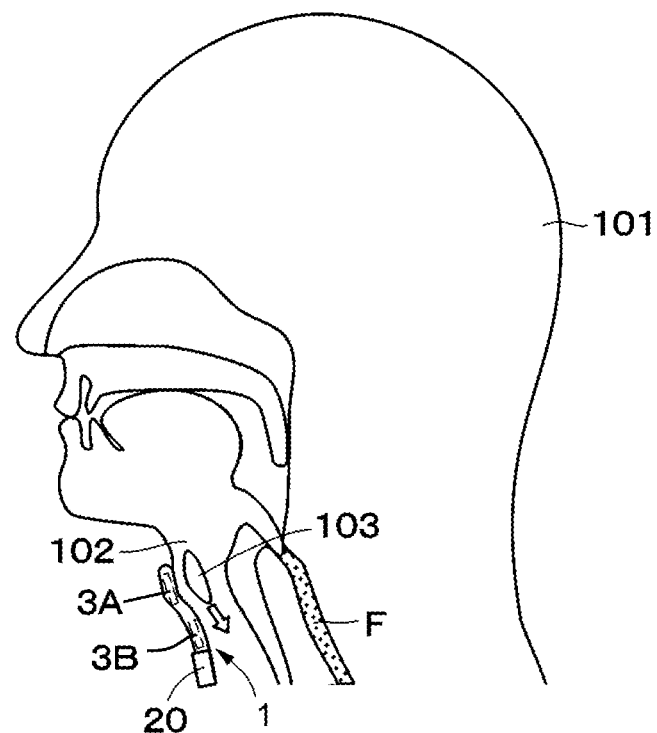
FIG. 8 is an explanatory view illustrating the positional relationships between the thyroid cartilage and the sensing portions of the swallowing sensor during transition from the pharyngeal stage to an esophageal stage.
Figure 9:
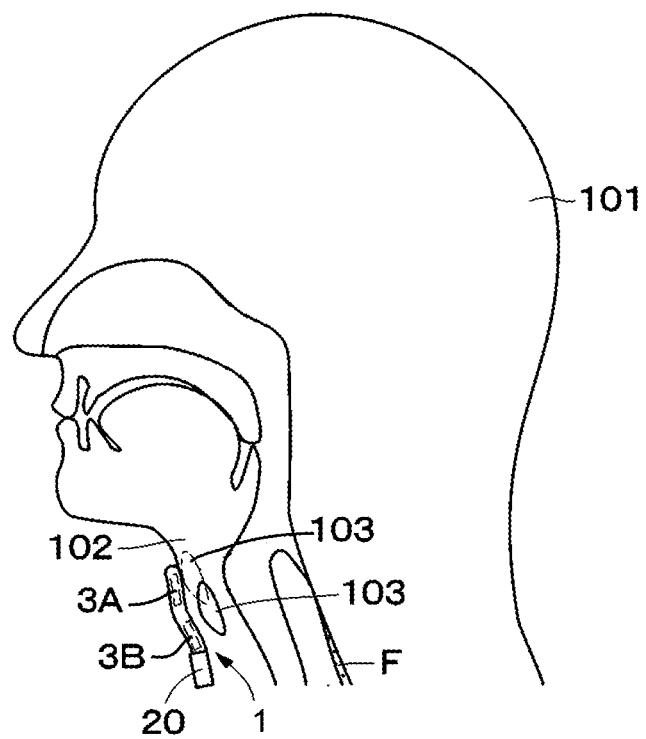
FIG. 9 is an explanatory view illustrating the positional relationships between the thyroid cartilage and the sensing portions of the swallowing sensor in the esophageal stage.

In a subsequent pharyngeal stage, the subject 101 delivers the food F from the oral cavity to the pharynx. As illustrated in FIG. 7, the thyroid cartilage 103 located under the lower sensing portion 3B moves to a position under the upper sensing portion 3A during the swallowing action. In a subsequent esophageal stage illustrated in FIG. 8 and FIG. 9, the subject 101 delivers the food F from the pharynx to the esophagus. At this time, the respiratory tract is closed and therefore the food F does not enter the respiratory tract. The food F is delivered from the esophagus to the stomach.

During the swallowing action, waveform patterns differ between the displacement signal (low frequency component S2L$a$) from the lower sensing portion 3B and the displacement signal (low frequency component S1L$a$) from the upper sensing portion 3A. The output displacement speed components are maximum when the thyroid cartilage 103 moves upward (see FIG. 7). For example, when the thyroid cartilage 103 moves from the lower side to the upper side of the piezoelectric film sensor 3 as illustrated in FIG. 10 and FIG. 11, the significant peaks Pa1 and Pb1 in opposite directions occur in the displacement signal from the lower sensing portion 3B and the displacement signal from the upper sensing portion 3A (see FIG. 13).

Figure 12:
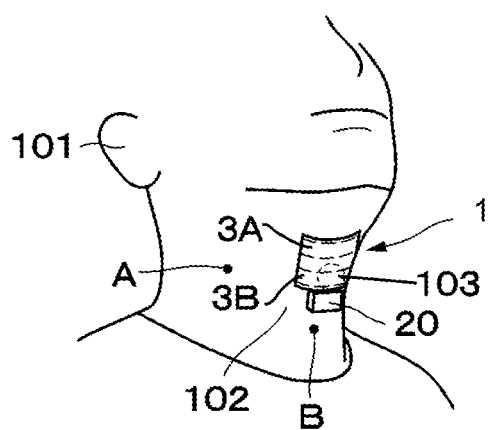
FIG. 12 is an explanatory view illustrating the positional relationships between the thyroid cartilage and the sensing portions of the swallowing sensor during an action of turning a face upward.

During the action of turning the face upward as illustrated in FIG. 12, the thyroid cartilage 103 does not move from the position under the lower sensing portion 3B. Therefore, the significant peaks are unlikely to occur in the output displacement speed components. Even if the significant peaks occur, the significant peaks in opposite directions do not occur in the displacement signal from the lower sensing portion 3B and the displacement signal from the upper sensing portion 3A. Since the displacement signals from the sensing portions 3A and 3B differ between the vertical movement of the neck and the swallowing action, erroneous detection along with the vertical movement of the neck can be suppressed.

Figure 10:
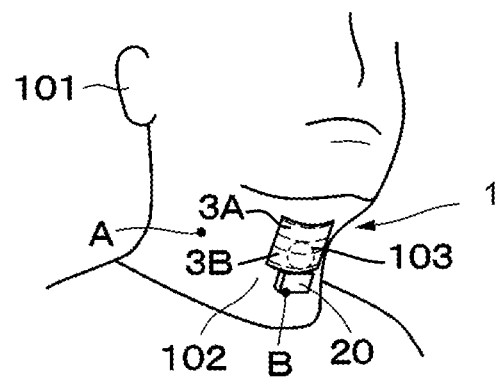
FIG. 10 is an explanatory view illustrating the positional relationships between the thyroid cartilage and the sensing portions of the swallowing sensor before a swallowing action.
Figure 11:
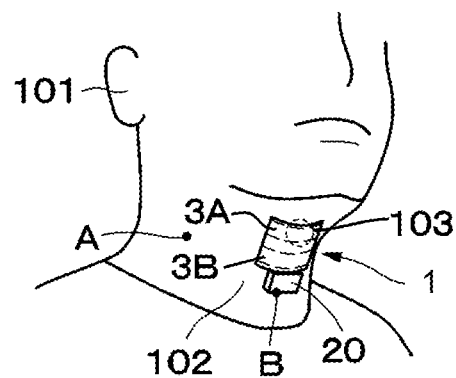
FIG. 11 is an explanatory view illustrating the positional relationships between the thyroid cartilage and the sensing portions of the swallowing sensor during the swallowing action.

FIG. 10 to FIG. 12 demonstrate that there is no significant difference between the swallowing action and the action of turning the face upward in terms of relative positional relationships of the thyroid cartilage 103 to a lateral neck portion A and a lower portion B of the anterior neck region 102. During the swallowing action, the thyroid cartilage 103 is displaced upward but the lateral neck portion A and the lower portion B of the anterior neck region 102 are not substantially displaced. If the sensor is fixed to the neck region by putting a retaining band around the neck as disclosed in Patent Document 1, the thyroid cartilage 103 is displaced upward relative to the posterior neck region when the subject 101 turns the face upward. Therefore, it is difficult to distinguish the movement of the thyroid cartilage 103 under the skin through the swallowing action from the movement of the thyroid cartilage 103 relative to the posterior neck region through the vertical movement of the neck. Thus, it is desirable that the fixing range of the swallowing sensor 1 be the skin on the thyroid cartilage 103 and the skin within a narrow range around the thyroid cartilage 103.

If the sensing region is a narrow range, the thyroid cartilage 103 falls out of the range of its sensing region when the thyroid cartilage 103 moves during the swallowing. Therefore, the swallowing sensor 1 covers the movement range of the thyroid cartilage 103 with the plurality of sensing portions 3A and 3B.

The swallowing sensor 1 includes the signal processing unit 23 configured to detect the movement of the thyroid cartilage 103 and make determination for the swallowing action based on the analog signals S1$a$ and S2$a$ from the plurality of sensing portions 3A and 3B. The plurality of sensing portions 3A and 3B can output the analog signals S1$a$ and S2$a$ having different waveform patterns in response to the movement (upward movement and forward movement) of the thyroid cartilage 103. Therefore, when the analog signals S1$a$ and S2$a$ are outputted from the plurality of sensing portions 3A and 3B, the signal processing unit 23 can detect the movement of the thyroid cartilage 103 and make determination for the swallowing action by comparing the features of the waveform patterns of the analog signals S1$a$ and S2$a$.

Specifically, the signal processing unit 23 makes the swallowing determination by making determination for the upward movement and the forward movement of the laryngeal prominence based on the analog signals S1$a$ and S2$a$ from the plurality of sensing portions 3A and 3B. Therefore, the signal processing unit 23 can make the swallowing determination depending on whether the peaks Pa1 and Pb1 associated with the upward movement of the laryngeal prominence and the peaks Pa2 and Pb2 associated with the forward movement of the laryngeal prominence occur in the analog signals S1a and S2a.

The piezoelectric film sensor 3 is formed by using the piezoelectric film 4. Therefore, the sensing portions 3A and 3B can be formed thin and light and the movement of the larynx including the thyroid cartilage 103 is not hindered. Further, discomfort of the patient can be reduced. In addition, the weight of the piezoelectric film sensor 3 per the attachment area can be reduced and therefore the peeling of the piezoelectric film sensor 3 off the skin of the neck region can be suppressed.

The signal processing unit 23 makes determination for the swallowing action by using the displacement components (low frequency components S1La and S2La) of the analog signals S1a and S2a outputted from the piezoelectric film sensor 3. Since the signal frequencies of the displacement components are low, the signal processing unit 23 can make determination for the swallowing action by using the displacement components of the digital signals S1Ld and S2Ld whose sampling frequencies are low.

When the signal processing unit 23 determines that the swallowing occurs, the signal processing unit 23 extracts the displacement components (digital signals S1Ld and S2Ld of the low frequency components S1La and S2La) and the sound components (digital signals S1Hd and S2Hd of the high frequency components S1Ha and S2Ha) of the pieces of signal data during the detected swallowing and wirelessly outputs the components. The swallowing analyzer 30 makes determination for the swallowing function based on the pieces of data on the displacement signals and the sound signals during the swallowing. Therefore, it is also possible to detect, for example, abnormal noise frequently observed in a swallowing function abnormality. Thus, the determination accuracy of the swallowing function (dysphagia) is improved.

Further, the frequency component having a frequency up to about 3 kHz at the minimum is required for the sound component. Therefore, the sampling frequency needs to be about 10 kHz. Thus, the data amount becomes enormous when the sound component is measured for a long time. When the swallowing sensor 1 determines that the swallowing occurs, the swallowing sensor 1 extracts the displacement components and the sound components of the pieces of signal data during the detected swallowing and wirelessly outputs the components. Therefore, there is no need to wirelessly output the displacement components and the sound components of the pieces of signal data constantly. It is only necessary to extract the displacement components and the sound components of the pieces of signal data only when the swallowing determination is made. Thus, it is possible to reduce the occurrence of the case in which the acquired data becomes enormous compared with the case in which the pieces of signal data are wirelessly output constantly.

In the embodiment described above, the amplified analog signal is separated into the low frequency component and the high frequency component. The present disclosure is not limited thereto and the digital signal obtained through the AD conversion may be separated into the low frequency component and the high frequency component. Further, the analog signal before amplification may be separated into the low frequency component and the high frequency component.

In the embodiment described above, the piezoelectric film sensor 3 is exemplified as the piezoelectric element. The piezoelectric element need not have the film shape but may have a bulk shape (massive shape). Further, the piezoelectric material for the piezoelectric element is not particularly limited as long as the piezoelectric material is a substance having piezoelectricity. For example, a material containing, as a main component, a compound having a wurtzite structure or a composite oxide having a perovskite structure ($ABO_3$) (perovskite composite oxide) may be used as the piezoelectric material for the piezoelectric element.

Examples of the compound having the wurtzite structure include aluminum nitride, gallium nitride, indium nitride, beryllium oxide, zinc oxide, cadmium sulfide, zinc sulfide, and silver iodide.

For example, at least one kind of element selected from among lead (Pb), barium (Ba), calcium (Ca), strontium (Sr), lanthanum (La), lithium (Li), and bismuth (Bi) may be employed as an A site of the perovskite structure ($ABO_3$) of the perovskite composite oxide. For example, at least one kind of element selected from among titanium (Ti), zirconium (Zr), zinc (Zn), nickel (Ni), magnesium (Mg), cobalt (Co), tungsten (W), niobium (Nb), antimony (Sb), tantalum (Ta), and iron (Fe) is employed as a B site of the perovskite structure ($ABO_3$).

Specific examples of the perovskite composite oxide include lead zirconate titanate [$Pb(Zr, Ti)O_3$] (referred to also as PZT), potassium tantalate niobate [$K(Ta, Nb)O_3$], barium titanate ($BaTiO_3$), and (Pb, La)(Zr, Ti)$O_3$ [such as lead titanate ($PbTiO_3$)].

In the embodiment described above, only the data on the displacement signal is acquired at the low sampling frequency at the start of operation of the swallowing sensor 1 to reduce power consumption. The present disclosure is not limited thereto. For example, the data on the displacement signal and the sound signal may be acquired at the high sampling frequency from the start of operation of the swallowing sensor 1.

Next, description is made of the disclosure incorporated in the embodiment described above. The swallowing analyzing system according to the present disclosure includes the piezoelectric element located within the range of the movement of the thyroid cartilage, which occurs along with the swallowing, and attached to the skin of the anterior neck region; the swallowing detector to be driven by the internal battery, configured to make determination for swallowing detection in real time based on the displacement signal that is the low frequency component of the signal outputted from the piezoelectric element, and configured to extract, when the swallowing is detected, the data on the signal during the detected swallowing and wirelessly output the data to the outside; and the swallowing analyzer configured to make determination for the swallowing function by receiving the data on the signal during the swallowing.

According to the present disclosure, the swallowing detector makes determination for swallowing detection by using the displacement signal on the thyroid cartilage. Therefore, the accuracy of swallowing determination increases. The swallowing detector makes determination for swallowing detection based on the displacement signal that is the low frequency component. Therefore, processing performance of high throughput is unnecessary for arithmetic processing in the determination for swallowing detection. Further, the swallowing detector includes the battery, and wirelessly outputs the data. Therefore, power supply and data output cables are unnecessary. Thus, the weights of the cables are eliminated, thereby being capable of reducing the occurrence of a case in which the piezoelectric element and the swallowing detector peel off the skin due to the weight.

Further, the swallowing detector makes the swallowing determination by processing measurement data. Every time determination is made that the swallowing is detected, the swallowing detector extracts the data on the signal during the swallowing and wirelessly outputs the data to the outside. Therefore, the wirelessly transmitted data is only the data during the swallowing. Thus, there is no need to continuously transmit a large amount of data. Accordingly, it is possible to reduce power consumption of, for example, the communication module and to use a small-size, low-height, and small-capacity battery as the internal battery.

Further, the swallowing analysis is performed by the external swallowing analyzer instead of the inside of the swallowing detector attached to the subject. A computer, a terminal, or the like in which internal analysis processing is rewritable may be used as the swallowing analyzer. Even if the swallowing analysis method is revised, the revised analysis method can be applied easily.

In the present disclosure, the swallowing detector acquires the displacement signal at the low sampling frequency. When a change that satisfies the predetermined condition is detected in the data on the displacement signal, the swallowing detector starts to acquire, at the high sampling frequency, the sound signal that is the high frequency component of the signal outputted from the piezoelectric element. When the swallowing is detected based on the displacement signal, the swallowing detector extracts the data on the displacement signal and the sound signal during the detected swallowing and wirelessly outputs the data to the outside.

According to the present disclosure, the data on the displacement signal is acquired at the low sampling frequency and, when the change that satisfies the predetermined condition is detected in the data on the displacement signal, the data on the sound signal is acquired at the high sampling frequency. Therefore, the data amount is normally small and high-speed processing is unnecessary. Thus, power consumption can be reduced. As a result, a small-capacity battery can be used as the internal battery.

Further, when the displacement around the thyroid cartilage starts to occur and a change that satisfies the predetermined condition (for example, the rate of change is equal to or higher than the threshold) starts to be detected in the data on the displacement signal, the data on the sound signal is acquired at the high sampling frequency. Therefore, the determination for swallowing detection can be made accurately by using not only the data on the displacement signal but also the data on the sound signal.

Further, only partial data with strong possibility of the swallowing involving the displacement around the thyroid cartilage is automatically extracted from the displacement signal and the sound signal. For example, even in measurement during sleep, it is possible to exclude unnecessary data indicating that the swallowing does not occur. Thus, there is no need to extract the swallowing from long-time data through ex-post data analysis.

In the present disclosure, the piezoelectric element is located within the range of the movement of the thyroid cartilage, which occurs along with the swallowing, is attached to the skin of the anterior neck region, includes the plurality of sensing portions in the longitudinal direction of the neck region, and individually outputs the signals along with the deformation of the plurality of sensing portions. The swallowing detector detects the movement of the thyroid cartilage and makes determination for the swallowing action based on the signals from the plurality of sensing portions.

According to the present disclosure, the piezoelectric element includes the plurality of sensing portions in the longitudinal direction of the neck region and outputs the signals along with the deformation of the plurality of sensing portions. Therefore, the plurality of sensing portions can output signals having different waveform patterns in response to the movement (upward movement and forward movement) of the thyroid cartilage. By using the signals from the plurality of sensing portions, the swallowing can be identified more easily than in the case in which a single sensing portion is used.

Further, the piezoelectric element is attached to the skin on the thyroid cartilage and includes the plurality of sensing portions in the longitudinal direction of the neck region. For example, at the time of nodding action or other neck actions that do not cause a change in the relative position between the thyroid cartilage and the skin on the thyroid cartilage (action of vertically moving the head), the relative position between the thyroid cartilage and the skin does not change. At the time of swallowing action, the relative position between the thyroid cartilage and the skin changes. Therefore, the signals from the sensing portions differ between the vertical movement of the neck and the swallowing action. Thus, erroneous detection along with the vertical movement of the neck can be suppressed.

In the present disclosure, the swallowing detector makes determination for the swallowing by making determination for the upward movement and the forward movement of the laryngeal prominence based on the signals from the plurality of sensing portions.

In the upward movement of the laryngeal prominence, peaks occur in the signals from the plurality of sensing portions because the laryngeal prominence moves upward. In the forward movement of the laryngeal prominence, peaks occur in the signals from the plurality of sensing portions because the laryngeal prominence moves forward. The swallowing detector can make determination for the swallowing by determining whether the peaks occur.

In the present disclosure, the piezoelectric element is formed by using the piezoelectric film.

According to the present disclosure, the piezoelectric element is formed by using the piezoelectric film. Therefore, the weight of the piezoelectric element per attachment area can be reduced. Thus, the sensing portions can be formed thin and light, and the movement of the larynx including the thyroid cartilage is not hindered. Further, discomfort of the patient can be reduced, and the peeling of the piezoelectric element off the skin of the neck region can be suppressed because the piezoelectric element is light.

In the present disclosure, the swallowing analyzer makes determination for the swallowing function based on the data on the displacement signal and the sound signal during the swallowing.

Therefore, it is also possible to detect, for example, abnormal noise frequently observed in a swallowing function abnormality. Thus, the determination accuracy of the swallowing function (dysphagia) is improved.

In the embodiments described above, description is made using the piezoelectric film sensor 3 as the sensor portion 2. The sensor portion may be a strain sensor. The strain sensor (strain detecting element) is described below.

As illustrated in FIGS. 14 to 17, a strain sensor 100*a* of a first embodiment is a strain sensor including a sensor unit 4*a* and a fixing member 6*a*.

The sensor unit 4a includes a sensor sheet 41a, a body 42a, and a connecting portion 43a. The sensor sheet 41a includes a detecting portion 45a configured to detect strain in a predetermined direction, and fixing portions 46a and 47a located at both ends of the detecting portion 45a. The sensor sheet 41a is coupled, via the connecting portion 43a, to the body 42a configured to process signals outputted from the detecting portion 45a.

The fixing member 6a has a first principal surface and a second principal surface that face each other. A tensile load of the fixing member 6a is larger than a tensile load of the detecting portion 45a of the sensor sheet 41a.

The sensor unit 4a is fixed to the first principal surface of the fixing member 6a by attaching the sensor sheet 41a and the body 42a to the fixing member 6a. The sensor sheet 41a is fixed in a state in which the entire sensor sheet 41a overlaps the first principal surface of the fixing member 6a. That is, the fixing member 6a exists so as to overlap the entire sensor sheet 41a in a plan view. The plan view means that the strain sensor is viewed orthogonally to the principal surface of the fixing member.

The strain sensor 100a of the first embodiment is used by attaching the second principal surface of the fixing member 6a to a measurement target object so that the detecting portion 45a of the sensor sheet 41a is located in a measurement region of the measurement target object.

The detailed structures of the sensor unit 4a, the fixing member 6a, and the strain sensor 100a are described below.
(Sensor Unit)

As described above, the sensor unit 4a includes the sensor sheet 41a, the body 42a, and the connecting portion 43a.

The sensor sheet 41a includes a base 51a having a first principal surface and a second principal surface that face each other, and a conductor 52a provided on the first principal surface of the base 51a.

The constituent material for the base 51a is preferably an expansible and contractible material having a low elastic modulus. The material preferably contains an expansible and contractible material having a low elastic modulus, such as polyurethane, acrylic, or a silicone resin.

The thickness of the base 51a is not particularly limited. The thickness may be preferably 10 µm or more and 200 µm or less, more preferably 20 µm or more and 100 µm or less, even more preferably 30 µm or more and 50 µm or less.

The conductor 52a extends to the connecting portion 43a and the body 42a. That is, the conductor 52a includes a terminal conductor 52a4 provided on the body 42a, a wiring conductor 52a3 provided on the connecting portion 43a, a fixing conductor 52a2 provided on the fixing portion 46a, and a detecting conductor 52a1 provided on the detecting portion 45a. Specifically, the conductor 52a extends from the body 42a to the detecting portion 45a of the sensor sheet via the connecting portion 43a and the fixing portion 46a of the sensor sheet, extends leftward from the right end of the detecting portion 45a, and returns to the right end while being folded near the center of the detecting portion 45a. The right side of the drawing is defined as a right side of the detecting portion 45a. The conductor 52a that returns to the right end extends to the body 42a via the fixing portion 46a of the sensor sheet and the connecting portion 43a. The folded portions of the conductor 52a are arranged parallel to each other. The detecting conductor 52a1 expands or contracts in a lateral direction in conformity with expansion or contraction of the detecting portion 45a in the lateral direction. The resistance value of the detecting conductor 52a1 changes in response to the change in the length of the detecting conductor 52a1. By detecting the change in the resistance value of the detecting conductor 52a1, the expansion/contraction amount of the detecting portion 45a, that is, strain of the measurement target object can be detected. That is, the detecting conductor 52a1 constitutes a sensing portion 52a11.

The constituent material for the detecting conductor 52a1 of the conductor 52a is preferably a material that greatly changes in the resistance value in response to expansion or contraction. It is preferable to form the detecting conductor 52a1 by using a mixture containing metal powder such as silver (Ag) or copper (Cu) and an elastomeric resin such as silicone. When the detecting conductor 52a1 is formed by using the mixture of the metal powder and the resin, the number of contacts between particles of the metal powder increases or decreases and the distance between the particles of the metal powder increases through the expansion or contraction of the detecting portion 45a. Therefore, it is possible to increase the rate of increase or decrease in the resistance value with respect to displacement. When the detecting conductor 52a1 is formed by using the mixture of the metal powder and the resin, breakage due to deformation can be prevented by expansion and contraction properties of the resin.

The constituent material for the portions of the conductor 52a other than the detecting conductor 52a1, specifically, the fixing conductor 52a2, the wiring conductor 52a3, and the terminal conductor 52a4, may be the same constituent material as that for the detecting conductor 52a1 or may be a constituent material different from that for the detecting conductor 52a1. If the conductor 52a other than the detecting conductor 52a1 is formed of the same material as that for the detecting conductor 52a1, the detecting conductor 52a1 and the conductor 52a other than the detecting conductor 52a1 can collectively be formed in one step. Therefore, the manufacture can be performed at low costs. If the conductor 52a other than the detecting conductor 52a1 is formed of a constituent material different from that for the detecting conductor 52a1, the increase or decrease in the resistance value with respect to the displacement of the detecting conductor 52a1 is made more significant and the breakage due to the expansion or contraction is prevented. In addition, the conductor 52a other than the detecting conductor 52a1 can be formed of a material having a low resistance. Thus, strain can be detected with higher accuracy.

In the strain sensor 100a of the first embodiment, five conductors 52a are arranged. That is, the strain sensor 100a includes a plurality of sensing portions 52a11 to 52a15. The sensing portions 52a11 to 52a15 are arranged parallel to each other in the detecting portion 45a at regular intervals in a vertical direction. The vertical direction means a direction from top to bottom in FIG. 14 and FIG. 15. By providing the plurality of detecting portions, strain can be detected in a wider range or the accuracy can further be increased if the detection is performed in a range of the same size.

In this embodiment, the sensing portions 52a11 to 52a15 are arrayed in the longitudinal direction of the neck region (vertical direction) in a state in which the strain sensor 100a is attached to the anterior neck region 102 of the subject 101. Specifically, the sensing portions 52a11 to 52a15 are arranged from the upper side to the lower side so as to cover the thyroid cartilage 103. The sensing portions 52a11 to 52a15 are electrically isolated from each other and individually output signals.

The detecting portion 45a is a region where a change in the shape of the measurement target object is measured. The outside dimension of the detecting portion 45a is set in consideration of the range of the measurement region and the followability of the detecting portion 45a is set in consideration of the flexibility of the measurement target object.

The detecting portion 45a includes a plurality of slits 53a provided in a direction intersecting the direction of expansion and contraction of the detecting portion. By providing the slits 53a in the detecting portion 45a, the detecting portion 45a has a shape and structure in which the detecting portion 45a is deformed more easily than the periphery. Thus, the followability of the detecting portion 45a can be increased.

Figure 14:
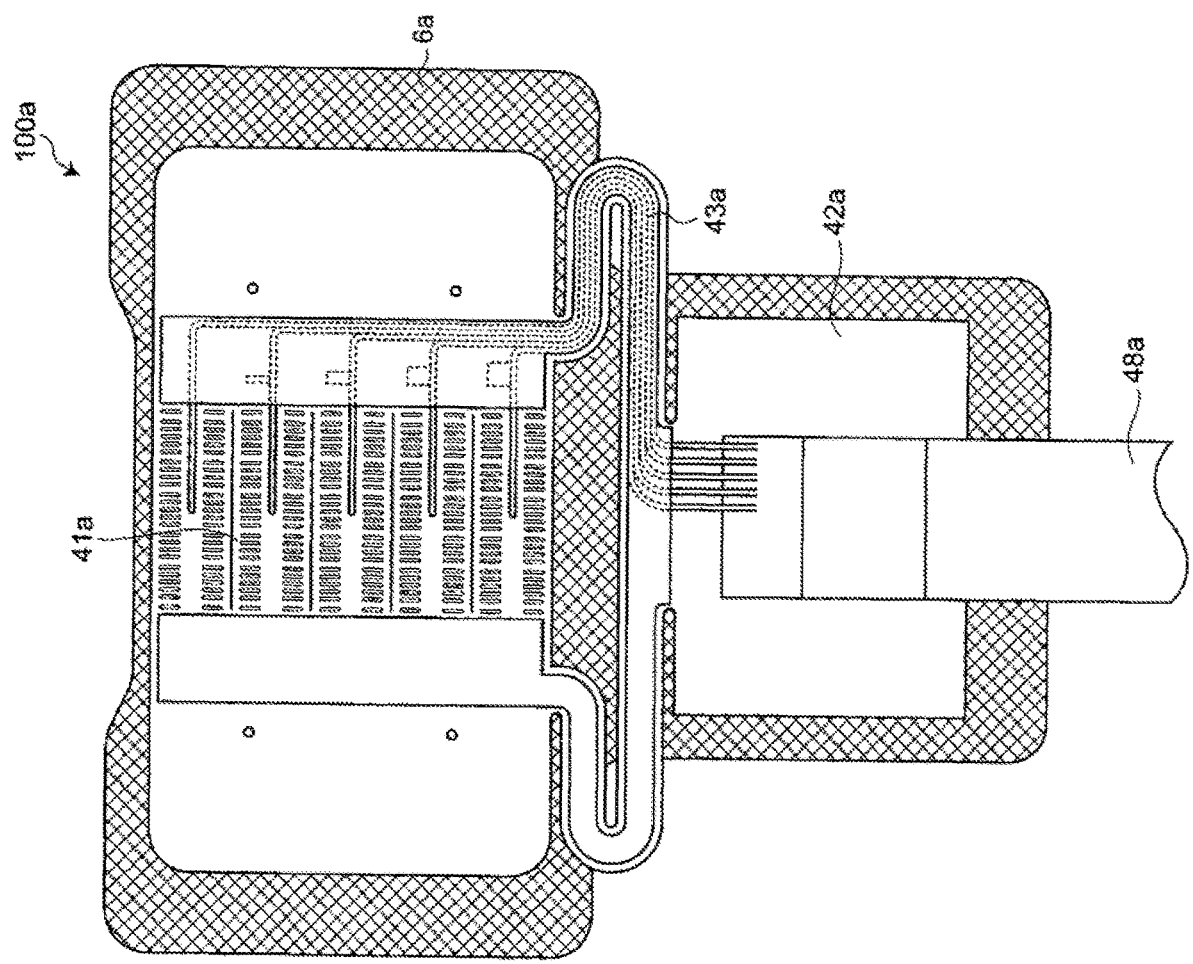
FIG. 14 is an explanatory view illustrating a strain sensor according to an embodiment of the present disclosure.

In the strain sensor 100a of the first embodiment, as illustrated in FIG. 14, the detecting portion 45a includes the sensing portion 52a11 constituted by the detecting conductor 52a1, and a low elastic modulus portion formed so as not to restrain the deformation of the detecting portion in response to strain and not to restrain the deformation of the measurement target object. The "low elastic modulus" in a case of expressing the low elastic modulus in the low elastic modulus portion or changing into the low elastic modulus herein means that the elastic modulus is lower than those of the fixing portions 46a and 47a.

Figure 15:
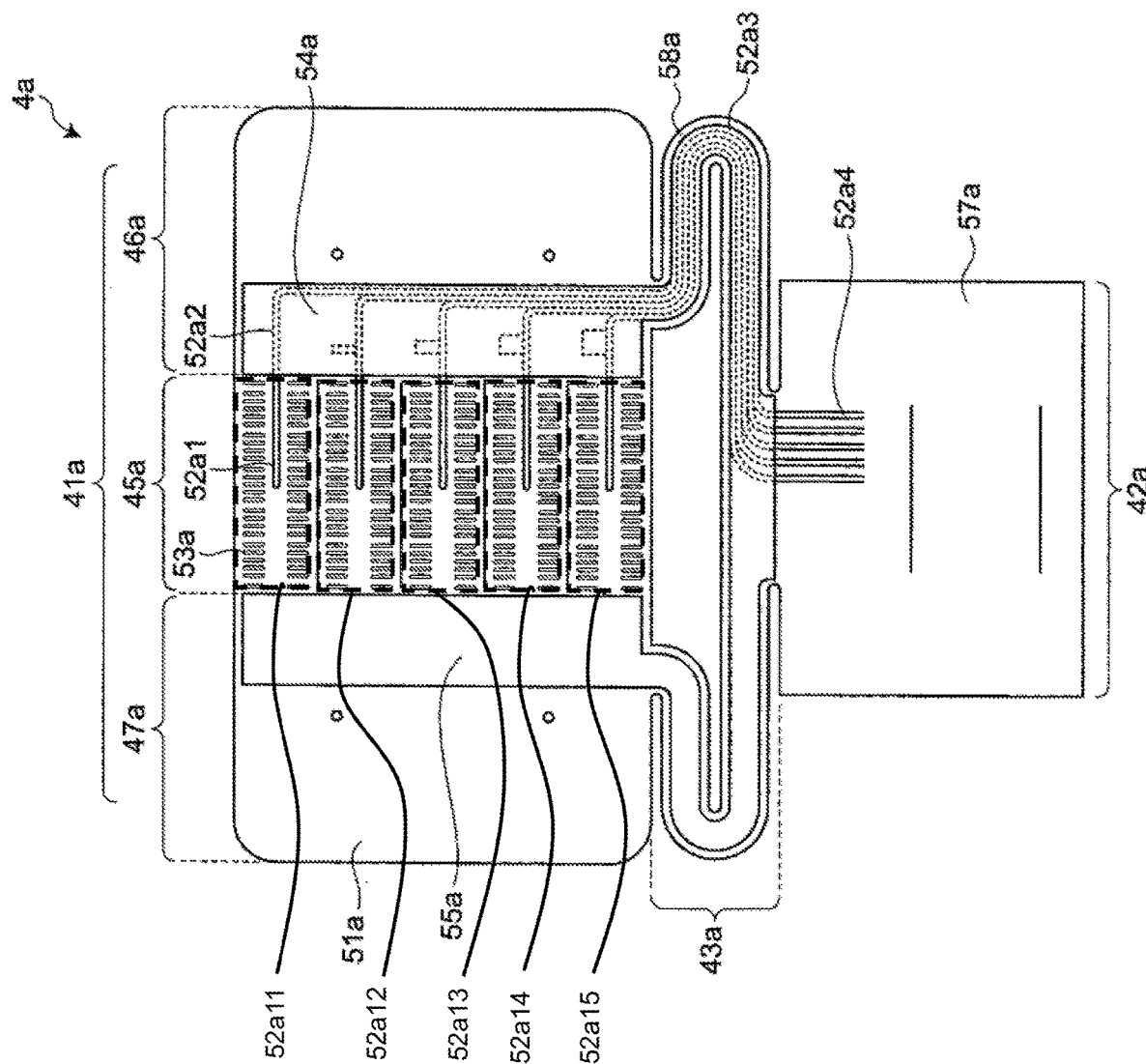
FIG. 15 is a cross-sectional view illustrating the strain sensor that is shown in FIG. 14.
Figure 16:
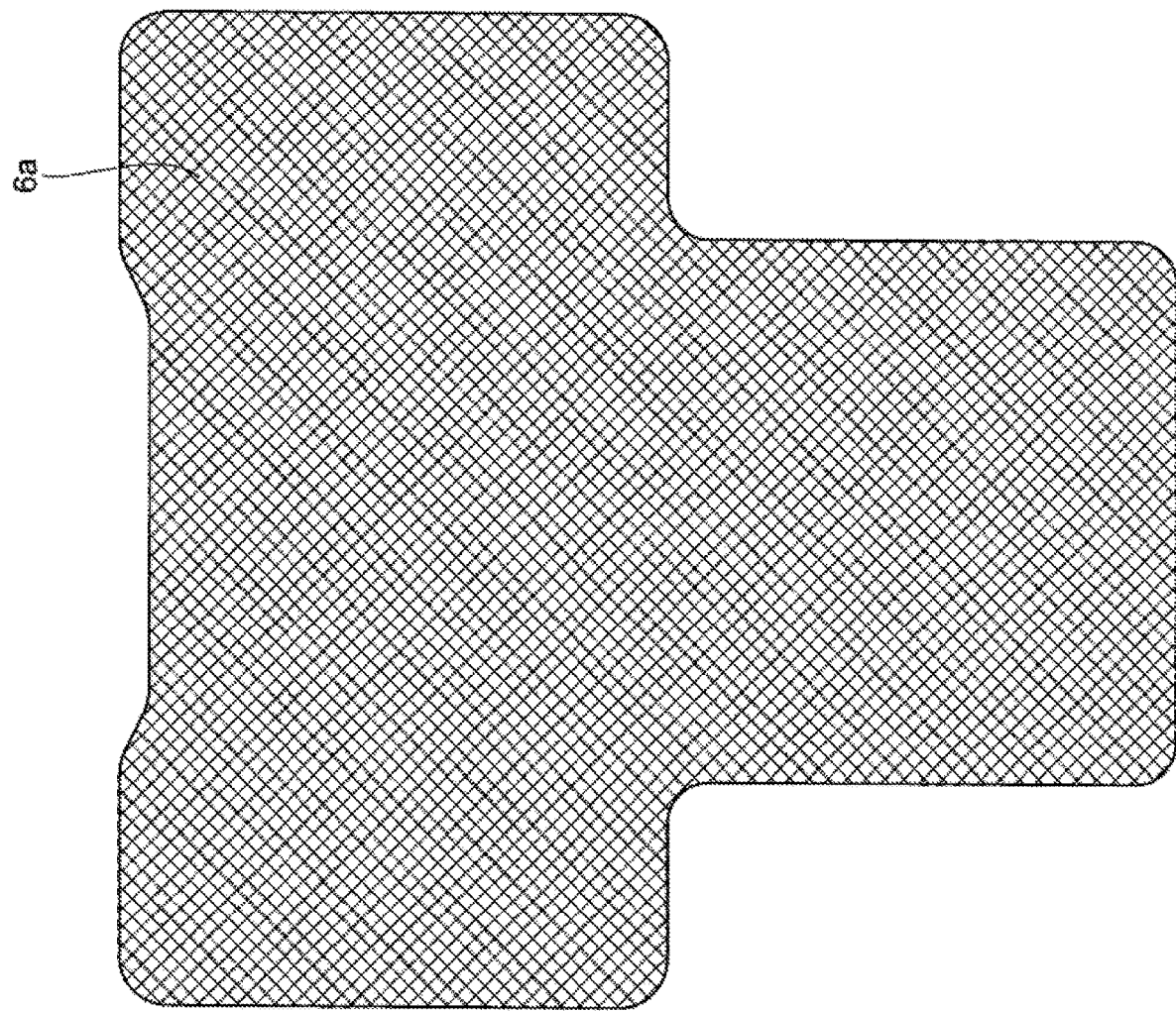
FIG. 16 is an explanatory view illustrating a fixing member of the strain sensor according to an embodiment of the present disclosure.

The fixing portions 46a and 47a support the detecting portion 45a so that, when the measurement region of the measurement target object expands or contracts, the detecting portion 45a expands or contracts in response to the expansion or contraction. In the strain sensor 100a of the first embodiment, the fixing portions 46a and 47a are provided on both sides of the detecting portion 45a in the direction of expansion and contraction of the detecting conductor 52a1 (that is, the detecting portion). The fixing portions 46a and 47a include confinement portions 54a and 55a so that, when the measurement region of the measurement target object expands or contracts, the strain corresponding to the expansion or contraction of the measurement region can be detected without being influenced by expansion or contraction of regions other than the measurement region. As illustrated in FIG. 15, the confinement portions 54a and 55a are provided in the fixing portions 46a and 47a, respectively. It is preferable that the confinement portions 54a and 55a be provided close to the detecting portion 45a. Thus, the strain in the measurement region of the measurement target object can accurately be measured while reducing the influence of portions other than the measurement region.

The body 42a includes a base 57a and the terminal conductor 52a4. The terminal conductor 52a4 is provided on one principal surface of the base 57a.

The constituent material for the base 57a is not particularly limited and may be the same material as the constituent material for the base 51a, such as polyurethane, acrylic, or a silicone resin.

The connecting portion 43a includes a base 58a and the wiring conductor 52a3. The wiring conductor 52a3 is provided on one principal surface of the base 58a. The connecting portion 43a is provided to couple the sensor sheet 41a to the body 42a and to electrically connect the detecting conductor 52a1 of the sensor sheet 41a to the terminal conductor 52a4 of the body 42a.

(Fixing Member)

The fixing member 6a is a sheet-shaped member having the first principal surface and the second principal surface that face each other.

The tensile load of the fixing member 6a is larger than the tensile load of the sensor sheet 41a. That is, the fixing member 6a is less stretchable than the sensor sheet 41a. With this structure, the degrees of buffering of movement by an interposed object having flexibility are equalized. Thus, variations in strain measurement results can be reduced. For example, if an articulation or cartilage is measured, movement is detected by the sensor with superficial skin interposed therebetween. Even if the movement of the articulation or cartilage is the same, the followability of the sensor differs due to individual differences in the flexibility of the skin, the shape of crease, or the like. Thus, different measurement results may be obtained. With the strain sensor disclosed herein, the variations in the measurement results can be reduced even if individual differences are present.

Examples of the constituent material for the fixing member 6a include a rubber and a sponge.

Examples of the rubber include a urethane rubber and a silicon rubber.

Examples of the sponge include a nitrile rubber sponge (NBR sponge), a chloroprene rubber sponge (CR sponge), and an ethylene rubber sponge (EPDM rubber sponge). The sponge is preferably the chloroprene rubber sponge.

The sponge may be a closed-cell or open-cell sponge.

Figure 17:
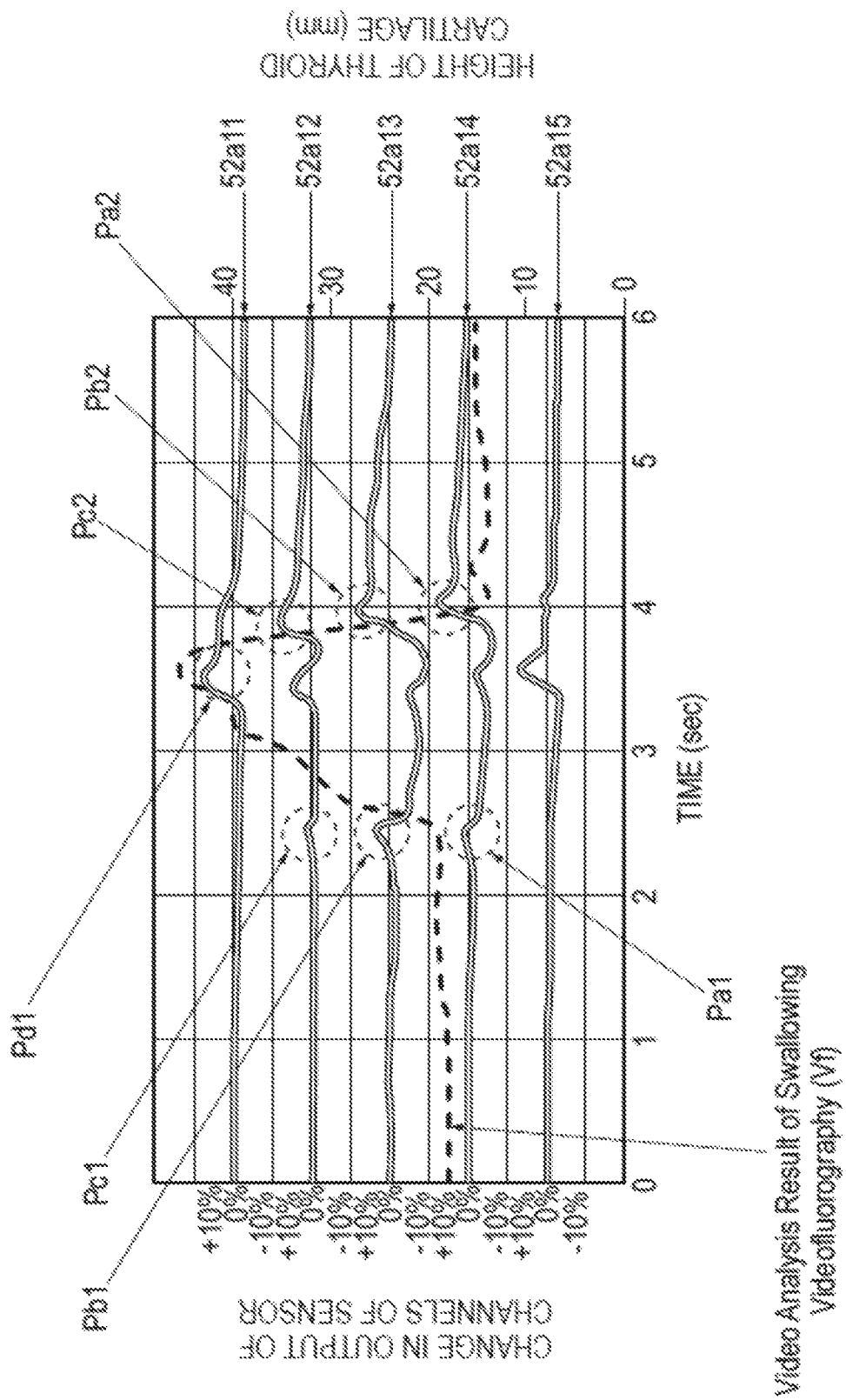
FIG. 17 illustrates an example of waveform patterns during swallowing, which are obtained by the strain sensor.

FIG. 17 illustrates an example of waveform patterns during swallowing, which are obtained by the strain sensor. The solid lines represent signals obtained by the sensing portions 52a11 to 52a15. The broken line represents a video analysis result of swallowing videofluorography (VF). A peak of an increase in a sensor output value occurs when the sensor is strained in a stretching direction. Therefore, the peak indicates that the thyroid cartilage moves forward or backward at the corresponding sensing portion. The forward movement of the thyroid cartilage can be estimated based on the increase or decrease in the sensor output value. If the peaks of the sensing portions appear with time differences, it can be estimated that the thyroid cartilage moves upward or downward so as to pass the sensing portions in order of the time differences.

Specifically, as illustrated in FIG. 17, peaks Pa1, Pb1, and Pc1 occur in the sensing portions 52a14 to 52a12 around 2.5 seconds. Then, a peak Pd1 occurs in the sensing portion 52a11 around 3.5 seconds and peaks Pc2, Pb2, and Pa2 occur sequentially in the sensing portions 52a12, 52a13, and 52a14 around 4 seconds. To check this movement against the video analysis result of the swallowing videofluorography (VF), the movement matches with a state in which the thyroid cartilage moves upward from around 2.5 seconds to around 3.5 seconds and moves downward from around 3.5 seconds to around 4 seconds. At this timing of vertical movement, a bolus of food passes by the thyroid cartilage. Thus, it can be confirmed that the swallowing occurs. That is, swallowing behavior is started at the peak Pa1, the thyroid cartilage ascends at Pb1, Pc1, and Pd1, and the thyroid cartilage descends at the peaks Pd1, Pc2, Pb2, and Pa2 to return to the initial position. Thus, it is understood that the swallowing is completed. The swallowing determination can be made based on the time differences among the peaks in the sensing portions.

1 swallowing sensor
2 sensor portion
3 piezoelectric film sensor (piezoelectric element)
3A, 3B sensing portion
4 piezoelectric film
5, 6 first and second electrode films
10 attachment member
20 body (swallowing detector)
21, 22 pre-processing unit
21B, 22B LPF
21C, 22C HPF
23 signal processing unit 24 memory
25 wireless communication module
26 battery
30 swallowing analyzer
S swallowing analyzing system

The invention claimed is:
1. A swallowing sensor, comprising:
a piezoelectric element configured to attach to skin of an anterior neck region in which thyroid cartilage moves during swallowing;
a swallowing detector driven by an internal battery, the swallowing detector being configured to:
  detect swallowing in real time based on directions of a plurality of peaks of a displacement signal, based on an occurrence of a first downward and a first upward peak within a first predetermined time, based on an occurrence of a second upward peak and a third upward peak that are each broader than the first upward peak within a second predetermined time, and based on an occurrence of a third downward peak and a fourth downward peak within a third predetermined time, the displacement signal being a low frequency component of an output from the piezoelectric element, and
  when the swallowing is detected, extract first data from the displacement signal during the detected swallowing and wirelessly output the first data.
2. The swallowing sensor according to claim 1,
wherein the piezoelectric element comprises a plurality of sensing portions in a longitudinal direction of the neck region, each of the sensing portions being configured to individually output signals in accordance with their deformation during swallowing, and
wherein the swallowing detector is configured to detect swallowing based on the signals from the plurality of sensing portions.
3. The swallowing sensor according to claim 2, wherein the swallowing detector is configured to detect swallowing by detecting upward movement and forward movement of a laryngeal prominence based on the signals from the plurality of sensing portions.
4. The swallowing sensor according to claim 1, wherein the piezoelectric element is a piezoelectric film.
5. A swallowing analyzing system, comprising:
the swallowing sensor according to claim 1, and
a swallowing analyzer configured to receive the first data from the swallowing sensor during the swallowing, and determine a swallowing function based on the received first data.
6. The swallowing analyzing system according to claim 5,
wherein the swallowing detector is further configured to detect swallowing based on a sound signal, and
wherein the swallowing analyzer is further configured to extract second data from the sound signal during the detected swallowing and wirelessly output the second data, and to determine the swallowing function based on the first data and the second data.
7. The swallowing sensor according to claim 1, wherein the swallowing detector is further configured to detect swallowing based on a sound signal.
8. The swallowing sensor according to claim 7,
wherein the swallowing detector is configured to acquire the displacement signal at a low sampling frequency, wherein, when a predetermined change is detected in the first data, the swallowing detector is configured to begin acquiring, at a high sampling frequency, the sound signal, the sound signal being a high frequency component of the output from the piezoelectric element,
wherein, when the swallowing is detected based on the displacement signal, the swallowing detector is further configured to extract second data from the sound signal during the detected swallowing and wirelessly output the second data, and
wherein the high sampling frequency is greater than the low sampling frequency.
9. A swallowing sensor, comprising:
a strain sensor configured to attach to skin of an anterior neck region in which thyroid cartilage during swallowing;
a swallowing detector driven by an internal battery, the swallowing detector being configured to:
  detect swallowing in real time based on directions of a plurality of peaks of a signal output from the strain sensor, based on an occurrence of a first downward and a first upward peak within a first predetermined time, based on an occurrence of a second upward peak and a third upward peak that are each broader than the first upward peak within a second predetermined time, and based on an occurrence of a third downward peak and a fourth downward peak within a third predetermined time; and
  when the swallowing is detected, extract first data from the signal during the detected swallowing and wirelessly output the first data.
10. The swallowing sensor according to claim 9,
wherein the strain sensor comprises a plurality of sensing portions in a longitudinal direction of the neck region, each of the sensing portions being configured to individually output signals in accordance with their deformation during swallowing, and
wherein the swallowing detector is configured to detect swallowing based on the signals from the plurality of sensing portions.
11. The swallowing sensor according to claim 10, wherein the swallowing detector is configured to detect swallowing by detecting upward movement and forward movement of a laryngeal prominence based on the signals from the plurality of sensing portions.
12. The swallowing sensor according to claim 9, wherein the strain sensor is a film sensor.
13. A swallowing analyzing system, comprising:
the swallowing sensor according to claim 9, and
a swallowing analyzer configured to receive the first data from the swallowing sensor during the swallowing, and determine a swallowing function based on the received first data.
14. The swallowing analyzing system according to claim 13,
wherein the swallowing detector is further configured to detect swallowing based on a sound signal, and
wherein the swallowing analyzer is further configured to extract second data from the sound signal during the detected swallowing and wirelessly output the second data, and to determine the swallowing function based on the first data and the second data.
15. The swallowing sensor according to claim 9, wherein the swallowing detector is further configured to detect swallowing based on a sound signal.
16. The swallowing sensor according to claim 15,
wherein, when a predetermined change is detected in the first data, the swallowing detector is configured to begin acquiring the sound signal, and wherein, when the swallowing is detected based on the signal output from the strain sensor, the swallowing detector is further configured to extract second data from the sound signal during the detected swallowing and wirelessly output the second data.

* * * * *